(12) United States Patent
Mixson

(10) Patent No.: US 7,772,201 B2
(45) Date of Patent: Aug. 10, 2010

(54) HIGHLY BRANCHED HK PEPTIDES AS EFFECTIVE CARRIERS OF SIRNA

(75) Inventor: Archibald Mixson, Rockville, MD (US)

(73) Assignee: "University of Maryland, Baltimore", Baltimore, MD (US)

( * ) Notice: Subject to any disclaimer, the term of this patent is extended or adjusted under 35 U.S.C. 154(b) by 231 days.

(21) Appl. No.: 11/718,342

(22) PCT Filed: Nov. 17, 2005

(86) PCT No.: PCT/US2005/041785

§ 371 (c)(1),
(2), (4) Date: May 1, 2007

(87) PCT Pub. No.: WO2006/060182

PCT Pub. Date: Jun. 8, 2006

(65) Prior Publication Data

US 2008/0171025 A1    Jul. 17, 2008

Related U.S. Application Data

(60) Provisional application No. 60/628,341, filed on Nov. 17, 2004.

(51) Int. Cl.
*A01N 43/04* (2006.01)
*A61K 31/70* (2006.01)

(52) U.S. Cl. .................................... 514/44
(58) Field of Classification Search .................. 514/44
See application file for complete search history.

(56) References Cited

U.S. PATENT DOCUMENTS

| | | | |
|---|---|---|---|
| 4,511,478 A | 4/1985 | Nowinski et al. | |
| 5,912,230 A | 6/1999 | Oppenheim et al. | |
| 5,965,434 A | 10/1999 | Wolff et al. | |
| 5,985,354 A | 11/1999 | Mathiowitz et al. | |
| 6,465,429 B1 | 10/2002 | Hancock et al. | |
| 6,506,559 B1 | 1/2003 | Fire et al. | |
| 7,070,807 B2 * | 7/2006 | Mixson | 424/484 |
| 7,163,695 B2 * | 1/2007 | Mixson | 424/486 |
| 7,465,708 B2 * | 12/2008 | Mixson | 514/14 |
| 2002/0151516 A1 | 10/2002 | Mixson | |
| 2003/0045465 A1 | 3/2003 | Mixson | |
| 2003/0165567 A1 | 9/2003 | Mixson | |
| 2004/0033602 A1 * | 2/2004 | Ford et al. | 435/455 |
| 2006/0211637 A1 * | 9/2006 | Scaria et al. | 514/44 |
| 2010/0028848 A1 * | 2/2010 | Parker et al. | 435/1.1 |

FOREIGN PATENT DOCUMENTS

| WO | WO/92/19195 A1 | 11/1992 |
|---|---|---|
| WO | WO/01/47496 A1 | 7/2001 |
| WO | WO/2004/048421 A2 | 6/2004 |

OTHER PUBLICATIONS

Chen et al. (Nucleic Acid Research 30:1338-1345, 2002).*

Rocheleau, C.E., et al. "Wnt signaling and an APC-related gene specify endoderm in early *C. elegans* embryos," Cell 1997; 90:707-716.

(Continued)

*Primary Examiner*—Brian Whiteman
(74) *Attorney, Agent, or Firm*—Castellano P.L.L.C.; Kristina Castellano

(57) ABSTRACT

The present invention is directed to methods of transfecting cells with siRNA, by contacting a transfection complex with one or more cells, where the transfection complex includes a transport polymer and siRNA. The transport polymer may include for example, $H^3K8b$ and/or structurally similar compounds. The invention is also directed to such transfection complexes, and to compositions that include such transfection complexes. The invention is further directed to methods of treating patients using the transfection complexes of the present invention.

| Polymer | Structure of Branched Polymers | Sequence of Domains |
|---|---|---|
| $H^3K8b$ | | H8=HHHHNHHHH<br>R=HHHKHHHKHHHK-HHH |
| $H^3K4b$ | | R=KHHHKHHHKHHH-KHHHK |
| $H^2K4b$ | | R=KHKHHKHHHKHH-KHHKHHKHK |
| HK4b | | R=KHKHKHKHKHKH-KHKHKHK |

13 Claims, 10 Drawing Sheets

OTHER PUBLICATIONS

Arenz, C., Schepers, U., "RNA interference: from an ancient mechanism to a state of the art therapeutic application?" Naturwissenschaften 2003; 90:345-359.

Coburn, GA, Cullen BR, "siRNAs: a new wave of RNA-based therapeutics," J. Antimicrob Chemother 2003; 51:753-756.

Fire, A., et al., "Potent and specific genetic interference by double-stranded RNA in *Caenorhabditis elegans*," Nature 1998; 391:806-811.

Hammond, S.M., et al., "An RNA-directed nuclease mediates post-transcriptional gene silencing in *Drosophila* cells," Nature 2000; 404:293-296.

Reynolds, A., et al., "Rational siRNA design for RNA interference," Nat. Biotechnol. 2004; 22:326-330.

Hammond, S.M., et al., "Argonaute2, a link between genetic and biochemical analyses of RNAi," Science 2001; 293:1146-1150.

Bernstein, E., et al., "Role for a bidentate ribonuclease in the initiation step of RNA interference," Nature 2001; 409:363-366.

Simeoni, F., et al., "Insight into the mechanism of the peptide-based gene delivery system MPG: implications for delivery of siRNA into mammalian cells," Nucleic Acids Res. 2003; 31: 2717-2724.

Chen, Q.R., et al, "Branched co-polymers of histidine and lysine are efficient carriers of plasmids," Nucleic Acids Res. 2001; 29:1334-1340.

Pollard, H., "Polyethylenimine but not cationic lipids promotes transgene delivery to the nucleus in mammalian cells," J. Biol. Chem. 1998; 273:7507-7511.

Zabner, J., et al., "Cellular and molecular barriers to gene transfer by a cationic lipid," J. Biol. Chem. 1995; 270:18997-19007.

Leng, Q., et al., "Highly branched HK peptides are effective carriers of siRNA," J. Gene Med. 2005; 7:977-986.

Opalinska, J.B., et al., "Nucleic-acid therapeutics: basic principles and recent applications," Nature Reviews, Jul. 2002, vol. 1, pp. 803-814.

PCT International Search Report and Written Opinion, PCT/US05/41785, 2006.

PCT International Preliminary Report on Patentability, PCT/US05/41785, 2007.

* cited by examiner

| Polymer | Structure of Branched Polymers | Sequence of Domains |
|---|---|---|
| H³K8b |  | H8=HHHHNHHHH<br>R=HHHKHHHKHHHKHHH |
| H³K4b |  | R=KHHHKHHHKHHHKHHHK |
| H²K4b |  | R=KHKHHKHHKHHKHHKHHKHK |
| HK4b |  | R=KHKHKHKHKHKHKHKHK |

| Polymer | Structure of Branched Polymers | Sequence of Domains |
|---|---|---|
| H³K8b (+RGD) OR (K+)H³K8b (+RGD) | | H³K8b(+RGD):<br>R=HHHKHHHKHHHKHHHK<br>(K+)H³K8b(+RGD):<br>R=KHHHKHHHKHHHKHHHK |
| H³K(G)8b | | H³K(G)8b:<br>R=HHHKHHHKHHHKHHHK |
| (-HHHK)H³K8b OR (-HHHK)H³K8b(+RGD) | | (-HHHK)H³K8b:<br>R=HHHKHHHKHHHK<br>X=C(O)NH2<br>(-HHHK)H³K8b(+RGD):<br>R=HHHKHHHKHHHK<br>X=RGD-C(O)NH2 |

HIGHLY BRANCHED HK PEPTIDES AS EFFECTIVE CARRIERS OF SIRNA

CROSS REFERENCE TO RELATED APPLICATIONS

The present application is a national stage application of, and claims priority to, PCT/US2005/041785 filed on Nov. 17, 2005, which claims the benefit of U.S. Provisional Patent Application 60/628,341 filed on Nov. 17, 2004, both of which are incorporated herein by reference in their entirety.

STATEMENT OF GOVERNMENT INTEREST

The present invention was developed with U.S. government funding from the National Institutes of Health, Grant No. CA096984. The government has certain rights in the invention.

FIELD OF THE INVENTION

The present invention is directed to methods of transfecting cells with siRNA by contacting a transfection complex with one or more cells. The present invention is also directed to the transfection complexes and compositions, thereof. The invention is further directed to methods of treating patients using the transfection complexes and compositions of the present invention.

BACKGROUND OF THE INVENTION

The use of small interfering RNA molecules (siRNA) is a potent new technology to silence genes and consequently their gene products. It has been reported that RNAi silences genes 10-fold more efficiently than antisense RNA alone. (Rocheleau C E, et al. Wnt signaling and an APC-related gene specify endoderm in early *C. elegans* embryos. *Cell* 1997; 90:707-716.) siRNAs have been used to study the role of proteins in signal transduction pathways and it has also been suggested that these molecules might be useful in treating a variety of diseases in which the causative protein is overexpressed. (Arenz C, Schepers U., RNA interference: from an ancient mechanism to a state of the art therapeutic application? *Naturwissenschaften* 2003; 90:345-359.; Coburn G A, Cullen B R. siRNAs: a new wave of RNA-based therapeutics. *J Antimicrob Chemother* 2003; 51:753-756.) To avoid non-specific gene silencing induced by longer double-stranded RNA, small interfering RNAs, a duplex of 21-23 nucleotides, have been used as mediators to degrade target mRNA. (Fire A, Xu S, Montgomery M K, Kostas S A, Driver S E, Mello C C. Potent and specific genetic interference by double-stranded RNA in *Caenorhabditis elegans. Nature* 1998; 391:806-811.) Once inside the cell, siRNA is incorporated into an RNA-induced silence complex (RISC), a protein-RNA complex that results in unwinding and strand separation of the RNA duplex. The antisense RNA then guides the activated RISC to anneal and cleave the target mRNA. (Hammond S M, Bernstein E, Beach D, Hannon G J. An RNA-directed nuclease mediates post-transcriptional gene silencing in *Drosophila* cells. *Nature* 2000; 404:293-296; Reynolds A, Leake D, Boese Q, Scaringe S, Marshall W S, Khvorova A. Rational siRNA design for RNA interference. *Nat Biotechnol* 2004; 22:326-330; Hammond S M, Boettcher S, Caudy A A, Kobayashi R, Hannon G J. Argonaute2, a link between genetic and biochemical analyses of RNAi. *Science* 2001; 293:1146-1150; Bernstein E, Caudy A A, Hammond S M, Hannon G J. Role for a bidentate ribonuclease in the initiation step of RNA interference. *Nature* 2001; 409:363-366.)

Both viral and nonviral carriers have been used to carry siRNA to their cytosolic mRNA target. (Simeoni F, Morris M C, Heitz F, Divita G. Insight into the mechanism of the peptide-based gene delivery system MPG: implications for delivery of siRNA into mammalian cells. *Nucleic Acids Res* 2003; 31:2717-2724.) To date, however, few peptide carriers have been developed that have proved effective for efficient siRNA delivery to eukaryotic cells (i.e., transfection).

There is a need in the art for pharmaceutical agent delivery systems having transfection efficiencies sufficient to deliver therapeutically effective amounts of siRNA into target cells. In particular, there is a need in the art for improved delivery systems capable of delivering siRNA into the interior of cells. There is also a need in the art for carriers that are stable in serum for delivery systems to be effective both in vitro and in vivo.

SUMMARY OF THE INVENTION

The present invention is directed to methods of transfecting cells with siRNA. In particular, the methods include contacting a transfection complex with one or more cells, where the transfection complex includes a transport polymer and siRNA. The transport polymer includes histidine and lysine. Examples of transport polymers include, but are not limited to, $H^3K8b$ (comprising SEQ ID NO: 14), $H^3K8b(+RGD)$ (comprising SEQ ID NOS: 14 and 15), and structurally similar analogs, having eight terminal branches and a histidine-rich domain, in particular, those polymers that are approximately the same size or somewhat smaller than $H^3K8b$ (comprising SEQ ID NO: 14). According to certain embodiments the cells may be selected from transformed, recombinant, malignant, or primary cell lines.

The methods of the present invention may also include forming a transfection complex. The methods may further include allowing the transfection complex to stand for about 15 minutes to about one and one half hours at approximately room temperature before contacting the transfection complex with cells.

The invention is further directed to transfection complexes that include siRNA and a transport polymer that includes $H^3K8b$ (comprising SEQ ID NO: 14) or a structural analog thereof. The present invention is further directed to compositions that include such transfection complexes.

BRIEF DESCRIPTION OF THE DRAWINGS

The invention will be more readily understood with reference to the embodiments thereof illustrated in the attached figures, in which:

FIG. 1 depicts schematic structures of HK polymers discussed herein including certain HK polymers of the present invention, such as $H^3K8b$ (comprising SEQ ID NO: 14). In the figures, the three solid circles connected by the solid lines represent the three-lysine core of each polymer. The dashed lines separate important domains or groups within the polymer. In the highly branched polymer $H^3K8b$ (comprising SEQ ID NO: 14), from the lysine core outward, the order is as follows: (1) four histidine-rich domains (H8: HHHHNH-HHH) (SEQ ID NO: 10); (2) four lysines (represented by K); and (3) eight terminal HK branches designated by R (SEQ ID NOS 18, and 20-22, respectively in order of appearance). In the lesser branched polymers ($H^3K4b$ (comprising SEQ ID NO: 20), $H^2K4b$ (comprising SEQ ID NO: 21), and HK4b (comprising SEQ ID NO: 22)), there are four terminal HK branches emanating from the three-lysine core. Throughout this application, the term "H³K8b" (comprising SEQ ID NO: 14) refers to the structure depicted in FIG. 1, without the integrin ligand, RGD. Similarly, the term "H³K8b(-RGD)" (comprising SEQ ID NO: 14) refers to the structure without RGD.

FIG. 2 is a bar graph depicting the efficiency of several potential carriers (Lipofectamine, DOTAP, H³K8b (comprising SEQ ID NO: 14), H³K4b (comprising SEQ ID NO: 20), H²K4b (comprising SEQ ID NO: 21), and HK4b (comprising SEQ ID NO: 22)) of β-gal siRNA, for their ability to inhibit β-galactosidase (β-gal) expression in SVR-bag4 cells. H³K8b (comprising SEQ ID NO: 14) was the most effective carrier in reducing expression by 80%. Of the polymers with only 4 terminal branches (i.e., HK4b (comprising SEQ ID NO: 22), H²K4b (comprising SEQ ID NO: 21), and H³K4b (comprising SEQ ID NO: 20)), the polymer H³K4b (comprising SEQ ID NO: 20) was the most effective carrier of siRNA. The data represents the mean+standard deviation (S.D.) of three experiments. P<0.001, Control vs. H³K8b (comprising SEQ ID NO: 14) or H³K4b (comprising SEQ ID NO: 20); **, P<0.05, Control vs. Lipofectamine, H²K4b (comprising SEQ ID NO: 21), or HK4b (comprising SEQ ID NO: 22) (Multiple Comparisons versus Control Group (Bonferroni t-test)).

FIG. 3A depicts transfected SVR-bag4 cells using H³K8b(+RGD) (comprising SEQ ID NOS: 14 and 15) as part of the transfection complex. FIG. 3B depicts untreated control cells.

FIG. 4 is a bar graph depicting β-galactosidase inhibition using different ratios of polymer:siRNA (wt/wt). To determine an optimal polymer:siRNA (μg:μg) ratio for H³K8b (comprising SEQ ID NO: 14), SVR-bag4 cells were transfected with different ratios of the polymer and siRNA targeting β-galactosidase. After 48 h, the β-galactosidase activity was quantified as described in the Examples. Polymer:siRNA ratios of between about 3:1 and about 6:1 inhibited β-galactosidase expression more than other ratios. The data represents the mean+S.D. of three experiments.

FIG. 5 is a bar graph depicting inhibition of luciferase when different carriers are used. To test the ability of H³K8b (comprising SEQ ID NO: 14) as a carrier of other siRNAs, the malignant MDA-MB-435 cell line was co-transfected with luciferase expression plasmid in complex with SuperFect (2:1 carrier/nucleic acid ratio), together with a luciferase-targeting siRNA by H³K8b(+RGD) (comprising SEQ ID NOS: 14 and 15) (4:1), H³K4b (comprising SEQ ID NO: 20) (4:1), DOTAP (4:1) for 24 h. Luciferase activity was measured with a Turner 20/20 luminometer. β-galactosidase siRNA was used as a control siRNA, transfected by H³K8b (comprising SEQ ID NO: 14) at a ratio of 4:1. The data represents the mean+S.D. of three experiments. *, P<0.001, Control vs. H³K8b(+RGD) (comprising SEQ ID NOS: 14 and 15), H³K4b (comprising SEQ ID NO: 20), or DOTAP; **, P<0.01, H³K8b(+RGD) (comprising SEQ ID NOS: 14 and 15) vs. H³K4b (comprising SEQ ID NO: 20) or DOTAP (One way ANOVA with bonferroni t-test multiple comparison tests).

FIG. 6 depicts transfection efficiency in SVR-bag4 (a mouse endothelial cell line, transformed by SV virus, that expresses β-galactosidase), MDA-MB-435 (a malignant breast cancer cell line), and C6 cell lines. Cells were transfected with Cy3-labeled siRNA in complex with DOTAP (4:1), Lipofectamine (4:1) or H³K8b(+RGD) (comprising SEQ ID NOS: 14 and 15) (4:1); 4 h later, images were obtained with a fluorescence microscope 100×. FIG. 6 shows that cells transfected using H³K8b(+RGD) (comprising SEQ ID NOS: 14 and 15) as the carrier for Cy3-labeled siRNA had a greater uptake of Cy3-labeled siRNA.

FIG. 9 depicts the structure of these polymers (SEQ ID NOS 23, 20, 23, and 24 are shown respectively in order of appearance).

FIG. 10 is a bar graph showing that the addition of a single lysine to the terminal branches in (+K)H³K8b(+RGD) (comprising SEQ ID NO: 20) or the replacement of the histidine rich domain (H8) with a glycine in H³K(G)8b(+RGD) (comprising SEQ ID NOS: 14 and 15) significantly reduced the ability of these polymers as carriers of siRNA. The data represents the mean+S.D. of three experiments. *, P<0.001: Untreated vs. Oligofectamine, H³K8b (comprising SEQ ID NO: 14), (-HHHK)H³K8b (comprising SEQ ID NOS: 16 and 17), H³K8b(+RGD) (comprising SEQ ID NOS:

Figure 1:
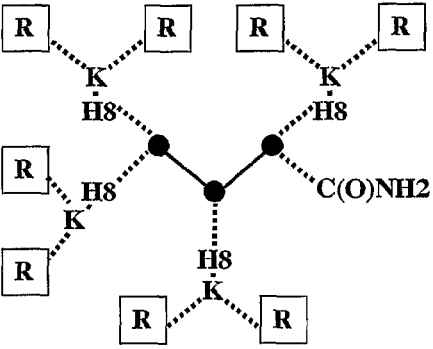
FIG. 1. Schematic structure of HK Polymers.
Figure 1:
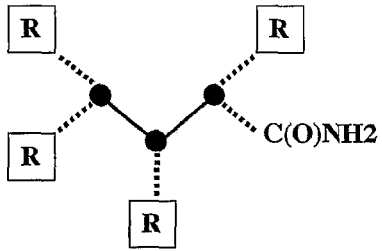
Figure 1:
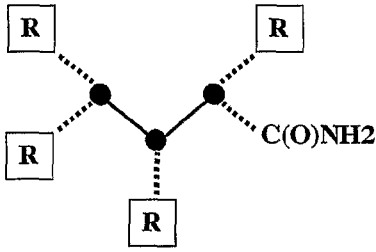
Figure 1:
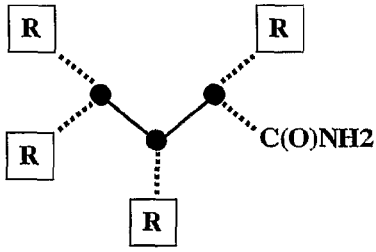

14 and 15), and (-HHHK)H³K8b(+RGD) (comprising SEQ ID NOS: 16 and 17); **, P<0.01: Oligofectamine vs. H³K8b (+RGD) (comprising SEQ ID NOS: 14 and 15) or (-HHHK) H³K8b(+RGD) (comprising SEQ ID NOS: 16 and 17) (one way ANOVA with Bonferroni multiple comparison tests). The ratio of HK polymers and Oligofectamine in complex with siRNA was 4:1 and 2:1 w/w respectively.

DETAILED DESCRIPTION OF THE INVENTION

The aspects, advantages and other features of the invention will become apparent in view of the following detailed description, which discloses various non-limiting embodiments of the invention. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose. Additionally, all of the citations herein are incorporated by reference in their entirety.

The present invention involves transfecting cells with siRNA. In particular, disclosed herein are novel siRNA transport complexes, comprising an unexpectedly advantageous transport polymer. Methods of the present invention include contacting a transfection complex with one or more cells, where the transfection complex includes a transport polymer and siRNA. The transport polymer is a carrier that includes histidine and lysine (an HK carrier).

As used herein, "a" or "an" may mean one or more. As used herein, "another" may mean at least a second or more.

The term "amino acid" is inclusive of the 20 common amino acids, as well as "nonstandard amino acids," for example, D-amino acids and chemically (or biologically) produced derivatives of "common" amino acids, including for example, β-amino acids.

A compound is "associated with" a second compound if the two compounds have formed a complex as a result of covalent or non-covalent interactions between the two compounds.

The term "copolymer" refers to a polymer that contains two or more types of units, regardless of the arrangement of units along the chain (random, alternating, block, graft), and regardless of its molecular structure (linear or branched). The term "histidine copolymer" means that the copolymer comprises histidine as one of its unit types. The term "transport polymer" means a polymer comprising the histidine copolymer of the invention.

The term "branch" is inclusive of any monomer or linear polymer (including co-polymer) thereof, which is covalently attached at least one end to the side group of a branching monomer. A branch which itself comprises one or more branching monomers is referred to as a "non-terminal branch". A branch which does not comprise a branching monomer is referred to as a "terminal branch". A "terminal branch" may include for example, the final division of branching of histidine or lysine to the n-terminal amino acid of the branch. The terminal branch may include a non-histidine or lysine amino acid (e.g., a cysteine or other linking agent), which aids in conjugating a stabilizing agent (such as PEG or HPMA) and/or a targeting ligand.

The term "branched polymer" is inclusive of any polymer comprising at least one backbone and at least one terminal branch. A branched polymer may further comprise one or more non-terminal branches.

The terms "HK peptide," "HK polymer," and "HK carrier" are intended to mean transport polymers, which include histidine and lysine, including the polymers encompassed by the present invention.

The term "in vivo" includes therapy based on injection, whether intravenous or local (e.g., intratumoral, intramuscular, subcutaneous, intratracheal, intravenous, or intraocular injection into organ or airway directly, injection into vessels of the organ, or aerosolized into airways). The term "in vivo" also includes therapy based on electroporation of tumor, tissue, or organ.

The term "lipid" is used as it is in the art and includes any chemical species having a hydrophobic and a hydrophilic portion. Hydrophilic characteristics typically derive from the presence of phosphato, carboxylic, sulfato, amino, sulfhydryl, nitro, and other like groups. Hydrophobicity may be conferred by cholesterol and derivatives thereof and by the inclusion of groups that include, but are not limited to, long chain saturated and unsaturated aliphatic hydrocarbon groups and such groups substituted by one or more aromatic, cycloaliphatic or heterocyclic group(s).

The term "non-cationic lipid" refers to any of a number of lipid species that exist either in an uncharged form a neutral zwitterionic form, or an anionic form at physiological pH. Such lipids include, for example diacylphosphatidylcholine, diacylphosphatidylethanolamine, ceramide, sphingomyelin, cephalin, cardiolipin, cerebrosides, DOPE, and cholesterol.

The term "cationic lipid" refers to any of a number of lipid species which carries a net positive charge at physiologic pH. Such lipids include, but are not limited to, DODAC, DOTMA, DDAB, DOSPER, DOSPA, DOTAP, DC-Chol and DMRIE. Additionally, a number of commercial preparations of cationic lipids are available which can be used in the invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic liposomes comprising DOGS from Promega Corp., Madison, Wis., USA).

The term "peptide" is inclusive of both straight and branched amino acid chains, as well as cyclic amino acid chains, which comprise at least 2 amino acid residues. The terms "peptide" and "polypeptide" are used interchangeably herein.

A "pharmaceutical agent" includes any therapeutic agent useful in preventing, delaying or reducing the severity of the onset of a disease, or in reducing the severity of an ongoing disease, or in enhancing normal physiological functioning, as well as diagnostic agents, for example, a marker gene (GFP, luciferase). A "pharmaceutical agent" may consist of one or more therapeutic agents, one or more diagnostic agents, or a combination of one or more therapeutic and one or more diagnostic agents.

As used herein, a "pharmaceutically acceptable" component (such as a salt, carrier, excipient or diluent) of a pharmaceutical agent delivery composition according to the present invention is a component which (1) is compatible with the other ingredients of the delivery composition in that it can be included in the delivery composition without eliminating the capacity of the composition to deliver the pharmaceutical agent; and (2) where the delivery composition is intended for therapeutic uses, is suitable for use with an animal (e.g., a human) without undue adverse side effects, such as toxicity, irritation, and allergic response. Side effects are "undue" when their risk outweighs the benefit provided by the pharmaceutical agent.

As used herein, the term "physiologic pH" is defined as a pH between about 7.2 and about 7.5.

As used herein, the term "recombinant" means a cell having genetically engineered DNA, which was prepared in vitro and includes DNA from the host organism or, more often, from a different species, genus, family, order or class as compared to the host organism.

The term "siRNA" is used as it is in the art, and includes a duplex of RNA (30 bases or less in each strand) that targets mRNA. siRNA may be chemically or enzymatically synthesized. siRNA in accordance with the present invention may be incorporated and then activated in RISC(RNA-induced silencing complex).

A "therapeutically effective amount" is an amount necessary to prevent, delay or reduce the severity of the onset of disease, or an amount necessary to arrest or reduce the severity of an ongoing disease, and also includes an amount necessary to enhance normal physiological functioning.

The word "transfect" is broadly used herein to refer to introduction of an exogenous compound, such as a polynucleotide sequence, into a prokaryotic or eukaryotic cell; the term includes, without limitation, introduction of an exogenous nucleic acid into a cell, which may result in a permanent or temporary alteration of genotype in an immortal or non-immortal cell line.

The present inventor developed novel branched carriers comprising histidine and lysine which are useful for transfection of plasmids. (See Chen Q R, Zhang L, Stass S A, Mixson A J. Branched co-polymers of histidine and lysine are efficient carriers of plasmids. *Nucleic Acids Res* 2001; 29:1334-1340.) In these branched co-polymers, the lysine and histidine component forms a complex with and partially neutralizes the negative charge of the plasmid DNA. In addition, the histidine component, with a pKa of about 6.0, buffers and aids in the release of plasmid DNA from endosomal vesicles. In general, HK peptides are ineffective for delivery of siRNA. In the present invention the inventor has further developed these carriers and has now developed additional novel, highly branched HK polymers that are unexpectedly effective carriers of siRNA. The HK polymers of the present invention are advantageous, for example, in that they are less toxic and provide a more efficacious delivery of siRNA than other polymers.

The HK polymers of the present invention may be useful, for example, for in vitro delivery of siRNA to the interior of a cell. These polymers may, however, also have in vivo applications. These methods all include contacting a transfection complex with one or more cells to deliver the siRNA. The transfection complex includes at least one transport polymer and siRNA. The transport polymer includes histidine and lysine.

In general, a cell to be transfected includes, but is not limited to, any animal, plant or bacterial cell that is susceptible to intracellular delivery of siRNA using the transfection complex of the present invention either in vitro or in vivo. For example, suitable cellular targets include, without limitation, epithelial cells, endothelial cells, keratinocytes, fibroblasts, muscle cells, hepatocytes, blood cells such as T lymphocytes, B lymphocytes, monocytes, macrophages, neutrophils, eosinophils, megalaryocytes, granulocytes, various stem or progenitor cells, in particular hematopoietic stem or progenitor cells, e.g., as obtained from bone marrow, umbilical cord blood, peripheral blood, fetal liver, and the like. In certain aspects, the cell is selected from the group consisting of lung cells, liver cells, endothelial cells, muscle cells, skin cells, hematopoietic stem cells and tumor cells.

According to certain embodiments, the cells include one or more cells selected from the group consisting of transformed, recombinant, malignant, and primary cell lines. By way of non-limiting example, cells according to the present invention may include one or more cells selected from SVR-bag4, MDA-MB-435, C6 and HUVEC (human umbilical endothelial vein) cell lines.

With plasmid-based therapy, nuclear import is important for transcription to occur and this appears to be a rate-limiting step in several cell lines. (Pollard H, Remy J S, Loussouarn G, Demolombe S, Behr J P, Escande D. Polyethylenimine but not cationic lipids promotes transgene delivery to the nucleus in mammalian cells. *J Biol Chem* 1998; 273:7507-7511; Zabner J, Fasbender A J, Moninger T, Poellinger K A, Welsh M J. Cellular and molecular barriers to gene transfer by a cationic lipid. *J Biol Chem* 1995; 270:18997-19007.) Because nuclear import is unnecessary for siRNA to degrade its target mRNA, it is believed that the polymers of the present invention will be effective as carriers of siRNA in most cell lines.

Methods of transfecting cells in accordance with the present invention may also include forming the transfection complex and allowing the transfection complex to stand for about 15 minutes to about 1½ hours, or from about 15 to about 45 minutes at approximately room temperature before contacting the transfection complex with cells.

Transport polymers that include histidine and lysine in accordance with the present invention include one or more HK carriers that are effective for transporting siRNA, including for example, polymers having between six and 10 terminal branches. According to certain embodiments, the transport polymer of the present invention includes eight terminal branches and a histidine-rich domain. According to certain embodiments, the transport polymer comprises a terminal branch having a sequence of -HHHKHHHKHHHKHHH-KHHH- (SEQ ID NO: 11) or a subsegment thereof. Non-limiting examples of transport polymers in accordance with the present invention include one or more polymers selected from H$^3$K8b (comprising SEQ ID NO: 14) and structural analogs, such as H$^3$K8b(+RGD) (comprising SEQ ID NOS: 14 and 15), H$^3$K8b (comprising SEQ ID NO: 14) including one or more other ligand(s), (-HHHK)H$^3$K8b (comprising SEQ ID NOS: 16 and 17), (-HHHK)H$^3$K8b(+RGD) (comprising SEQ ID NOS: 16 and 17), and the like.

Transport polymers of the present invention may optionally include one or more stabilizing agents. Suitable stabilizing agents would be apparent to those skilled in the art in view of this disclosure. Non limiting examples of stabilizing agents in accordance with the present invention include polyethyleneglycol (PEG) or hydroxypropylmethylacrylimide (HPMA).

Transport polymers of the present invention may optionally include one or more targeting ligands. Suitable targeting ligands would be apparent to those skilled in the art in view of this disclosure.

A number of patterns of HK polymers that might be effective for siRNA transport were isolated, developed and considered. Of the polymers with 4 branches, the repeating pattern of HHHK (SEQ ID NO: 12) (e.g., H$^3$K4b (comprising SEQ ID NO: 20)) on the terminal branch appears to augment uptake of siRNA more effectively than the repeating patterns of HHK (e.g., H$^2$K4b (comprising SEQ ID NO: 21)) or HK (e.g., HK4b (comprising SEQ ID NO: 22)) (See FIGS. 1 and 2 which depict the structures of such polymers and their effectiveness). As a result, the inventor adopted a similar pattern in constructing the highly branched H$^3$K8b (comprising SEQ ID NO: 14) and H³K8b(+RGD) (comprising SEQ ID NOS: 14 and 15) and found it to be highly effective for preparing carriers of siRNA.

H³K8b (comprising SEQ ID NO: 14) has eight terminal branches, and has a high percentage of histidines and a low percentage of lysines. Compared to HHK, the pattern HHHK (SEQ ID NO: 12) has an increased buffering capacity because of the higher ratio of histidines, and reduced binding because of the lower ratio of lysines. An increased number of histidines in the terminal branches that buffer the acidic endosomal compartment would allow endosomal lysis and escape of DNA from the endosomes. Similarly, the histidine rich domain in H³K8b (comprising SEQ ID NO: 14) would be expected to increase cytosol delivery by enhancing the buffering capacity of the polymer. Nevertheless, replacement of the histidine-rich domain with a glycine or a truncated histidine-rich domain (-HHKHH) (SEQ ID NO: 13) resulted in HK polymers that were ineffective carriers of siRNA. That the HK polymer with the truncated histidine rich domain was no more effective than the polymer with the glycine suggest that the buffering capacity of the histidine-rich domain may not be a dominant mechanism for this domain. Moreover, these results indicate that all the domains (the terminal branches and the histidine-rich domain) of the highly branched HK peptides are important for the development of an effective siRNA carrier.

Although the repeating pattern of HHK was present in H³K4b (comprising SEQ ID NO: 20) and H³K8b(+RGD) (comprising SEQ ID NOS: 14 and 15), N-terminal lysines were removed in the highly branched polymer, H³K8b (comprising SEQ ID NO: 14). Reduction in the number of lysines in the terminal branches of H³K8b may lead to decreased binding of siRNA and increase the amount of siRNA in the cytoplasm compared to that in the nucleus. By adding a single lysine to each terminal branch of H³K8b (comprising SEQ ID NO: 14) (eight lysines total per polymer), the efficacy of the new polymer ((+K)H³K8b(+RGD)) (comprising SEQ ID NO: 20) in reducing the target mRNA was significantly impaired compared to that of H³K8b(+RGD) (comprising SEQ ID NOS: 14 and 15). A smaller polymer sequence (i.e., those not having the added lysine to each terminal branch) that accomplishes siRNA transport is advantageous in synthesizing polymers more readily. The idea that binding modulates siRNA release is consistent with the finding that a carrier peptide with increased binding to siRNA is less effective as a carrier for siRNA. (Simeoni F, Morris M C, Heitz F, Divita G. Insight into the mechanism of the peptide-based gene delivery system MPG: implications for delivery of siRNA into mammalian cells. *Nucleic Acids Res* 2003; 31:2717-2724.). Nevertheless, the vast amount of HK carriers with varying abilities to bind nucleic acids were ineffective carriers of siRNA.

H³K8b(−RGD) in complex with siRNA is only smaller in size than the H²K4b/siRNA complex. The inventor discovered that, although varying the H³K8b(RGD)/siRNA ratio changed the zeta potential (a measure of a particle surface charge) from positive to negative charge, the transfection activity was minimally effected. In contrast, uptake of the complexes correlated more closely with transfection levels of the polyplexes. H²K4b (comprising SEQ ID NO: 21) augmented plasmid uptake and protein expression from transfected plasmids significantly more than H³K8b (comprising SEQ ID NO: 14) (or H³K8b(+RGD) (comprising SEQ ID NOS: 14 and 15)). In contrast, H³K8b (comprising SEQ ID NO: 14) increased siRNA uptake more effectively than other HK polymers or non-viral carriers tested (See FIG. 6). Although uptake of the nucleic acid by the HK carriers in most cases correlates with the desired effect of the nucleic acid, discrepancies between uptake and the effect of the nucleic acid may occur more often with plasmid-based than with siRNA-delivery systems.

Non-limiting examples of HK polymers according to the present invention include, but are not limited to, one or more polymers selected from the group consisting of H³K8b (comprising SEQ ID NO: 14), H³K8b(+RGD) (comprising SEQ ID NOS: 14 and 15), (-HHHK)H³K8b (comprising SEQ ID NOS: 16 and 17), and (-HHHK)H³K8b(+RGD) (comprising SEQ ID NOS: 16 and 17). Other modifications may be made by those skilled in the art within the scope of this invention. For example, ligands other than RGD, such as ligands that target other receptors, may be added to the polymer(s) within the scope of the present invention. Additionally, polymers in size between and including a 16mer H³K8b (comprising SEQ ID NO: 14) polymer and a 12mer (-HHHK)H³K8b (comprising SEQ ID NOS: 16 and 17) polymer are within the scope of the present invention. Further, a fifth or sixth amino acid may be removed from H³K8b (comprising SEQ ID NO: 14) and still be within the scope of the present invention.

The following are examples of nomenclature of certain compounds within the scope of the present invention. This nomenclature is based on the IUPAC's nomenclature for organic compounds.

---

H³K8b:

K[(HHHKHHHKHHHKHHH)₂(KHHHHNHHHHH)]- (SEQ ID NO: 14)
K[(HHHKHHHKHHHKHHH)₂(KHHHHNHHHHH)]- (SEQ ID NO: 14)
K[(HHHKHHHKHHHKHHH)₂(KHHHHNHHHHH)] (SEQ ID NO: 14)
H³K8b(+RGD):

K[(HHHKHHHKHHHKHHH)₂(KHHHHNHHHHH)]- (SEQ ID NO: 14)
K[(HHHKHHHKHHHKHHH)₂(KHHHHNHHHHH)]- (SEQ ID NO: 14)
K[(HHHKHHHKHHHKHHH)₂(KHHHHNHHHHH)](RGD) (SEQ ID NO: 15)
(-HHHK)H³K8b

[(HHHKHHHKHHH)₂(KHHHHNHHHHH)]- (SEQ ID NO: 16)
K[(HHHKHHHKHHH)₂(KHHHHNHHHHH)]- (SEQ ID NO: 17)
K[(HHHKHHHKHHH)₂(KHHHHNHHHHH)] (SEQ ID NO: 17)

---

The terminal branch of H³K8b (comprising SEQ ID NO: 14) and H³K8b(+RGD) (comprising SEQ ID NOS: 14 and 15) includes the following sequence: (HHHKHHHKHHHKHHH) (SEQ ID NO: 18). The terminal branch of (-HHHK) H³K8b (comprising SEQ ID NOS: 16 and 17) includes the following sequence: (HHHKHHHKHHH) (SEQ ID NO: 19). To the terminal branch and/or to its core of highly branched polymers, stabilizing agents (such as polyethyleneglycol (PEG) or hydroxypropylmethylacrylimide (HPMA)) and/or targeting ligands may be added optionally.

Polypeptides of the invention can be chemically synthesized and purified by techniques well know in the art. For example, branched polypeptides may be prepared by any method known in the art for covalently linking any naturally occurring or synthetic amino acid to any naturally occurring or synthetic amino acid in a polypeptide chain which has a side chain group able to react with the amino or carboxyl group on the amino acids so as to become covalently attached to the polypeptide chain. In particular, amino acids with a free amino side chain group, such as, but not limited to, diaminobutyric acid, lysine, arginine, ornithine, diaminopropionic acid and citrulline, can be incorporated into a polypeptide so that an amino acid can form a branch therewith, for example, by forming a polypeptide bond to the free amino side group, from that residue. Alternatively, amino acids with a free carboxyl side chain group, such as, but not limited to, glutamic acid, aspartic acid and homocitrulline, can be incorporated into the polypeptide so that an amino acid can form a branch therewith, for example, by forming a polypeptide bond to the free carboxyl side group, from that residue. The amino acid forming the branch can be linked to a side chain group of an amino acid in the polypeptide chain by any type of covalent bond, including, but not limited to, polypeptide bonds, ester bonds and disulfide bonds.

For example, but not by way of limitation, branched polypeptides can be prepared as follows: (1) the amino acid to be branched from the main polypeptide chain can be prepared as an N-α-tert-butyloxycarbo-nyl (Boc) protected amino acid pentafluorophenyl (Opfp) ester and the residue within the main chain to which this branched amino acid will be attached can be an N-Fmoc-α-γ-diaminobutyric acid; (2) the coupling of the Boc protected amino acid to diaminobutyric acid can be achieved by adding 5 grams of each precursor to a flask containing 150 ml DMF, along with 2.25 ml pyridine and 50 mg dimethylaminopyridine and allowing the solution to mix for 24 hours; (3) the polypeptide can then be extracted from the 150 ml coupling reaction by mixing the reaction with 400 ml dichlormethane (DCM) and 200 ml 0.12N HCl in a 1 liter separatory funnel, and allowing the phases to separate, saving the bottom aqueous layer and re-extracting the top layer two more times with 200 ml 0.12 N HCl; (4) the solution containing the polypeptide can be dehydrated by adding 2-5 grams magnesium sulfate, filtering out the magnesium sulfate, and evaporating the remaining solution to a volume of about 2-5 ml; (5) the dipolypeptide can then be precipitated by addition of ethyl acetate and then 2 volumes of hexanes and then collected by filtration and washed two times with cold hexanes; and (6) the resulting filtrate can be lyophilized to achieve a light powder form of the desired dipolypeptide. Branched polypeptides prepared by this method will have a substitution of diaminobutyric acid at the amino acid position which is branched. Branched polypeptides containing an amino acid or amino acid analog substitution other than diaminobutyric acid can be prepared analogously to the procedure described above, using the N-F-moc coupled form of the amino acid or amino acid analog.

Polypeptides of the transport polymer can also be encoded by viral DNA and be expressed on the virus surface. Alternatively, histidine could be covalently linked to proteins through amide bonds with a water soluble di-carboimide.

The HK transport polymer may also include a polypeptide—"synthetic monomer" copolymer. In these embodiments, the transport polymer backbone may comprise covalently linked segments of polypeptide and segments of synthetic monomer or synthetic polymer. The synthetic monomer or polymer may be biocompatible and/or biodegradable. Examples of synthetic monomers include ethylenically or acetylenically unsaturated monomers containing at least one reactive site for binding to the polypeptide. Suitable monomers as well as methods for preparing a polypeptide—"synthetic monomer" copolymer are described in U.S. Pat. No. 4,511,478, for "Polymerizable compounds and methods for preparing synthetic polymers that integrally contain polypeptides," by Nowinski et al, which is herein incorporated by reference. Where the transport polymer comprises a branched polymer, synthetic monomer or polymer may be incorporated into the backbone(s) and/or branch(es). Furthermore, a backbone or branch may include a synthetic monomer or polymer. Finally, in this embodiment, the branching monomers may be branching amino acids or branching synthetic monomers. Branching synthetic monomers may include for example, ethylenically or acetylenically unsaturated monomers containing at least one substituent reactive side-group.

A non-limiting example of siRNA in accordance with the present invention is siRNA that targets the Raf-1 sequence, 5'-AAUGUCCACAUGGUCAGCACC-3' (SEQ ID NO: 1). Other forms of siRNA are also encompassed by the present invention.

An ex vivo delivery method of the present invention may include for example, (i) removing a cell from a subject; (ii) introducing siRNA into a cell by contacting the cell with a delivery composition (transfection complex or composition comprising such a transfection complex) comprising siRNA and an HK polymer; and (iii) reintroducing the cell into the subject.

For in vivo therapies based on local injection (e.g., intratumoral, intramuscularly, into the peritoneal cavity, intracardiac, and aerosolized treatments) the overall content of histidine and non-histidine amino acids may render the branched transport polymer as a whole soluble in water. Where the branched transport polymer consists of amino acids, the branched transport polymer may be designed such that the content of histidine and non-histidine hydrophilic amino acids (i.e., amino acids having charged or uncharged polar side chains) renders the branched transport polymer soluble in water. In these embodiments, the histidine and non-histidine hydrophilic amino acids may represent at least 70%, at least 80%, at least 90%, at least 95%, or 100% of the amino acids in the branched transport polymer. Alternatively, a branched transport polymer that is otherwise insoluble in water may be rendered soluble in water by covalently attaching hydrophilic moieties (i.e., soluble ligands, soluble pharmaceutical agents, etc.) to the transport polymer. Where the pharmaceutical agent is a nucleic acid (generally negative charge) and non-covalent association with the transport polymer is desired, the non-histidine amino acids may be selected from the group consisting of amino acids with a side chain that are neutral hydrophilic (for example, serine, asparagine and glutamine) and amino acids with a side-group that carries a positive charge at physiological pH (e.g., lysine, ornithine, and arginine), and may be lysine. Where non-covalent association of a water soluble branched transport polymer and a water soluble pharmaceutical agent (for example, DNA) is contemplated, the HK transport polymer and the siRNA need not be associated prior to injection. While pre-injection formation of a pharmaceutical delivery complex is preferred, the transport polymer and siRNA may be administered (by local injection) sequentially (in either order) or simultaneously to form the pharmaceutical delivery composition at the site of injection.

The present invention is also directed to methods of forming a transfection complex, for example, by mixing siRNA with an HK transport polymer. In the transfection complex a ratio of the transport polymer to the siRNA may be about 0.5:1 (wt/wt) to about 24:1 (wt/wt), or about 0.5:1 (wt/wt) to about 24:1 (wt/wt), or about 0.5:1 (wt/wt) to about 6:1 (wt/wt), or about 3:1 (wt/wt) to about 6:1 (wt/wt).

The invention is further directed to transfection complexes, which include siRNA and an HK transport polymer. Transfection complexes in accordance with the present invention may include any of the HK polymers of the present invention.

Non-limiting examples of transfection complexes in accordance with the present invention include one or more polymers selected from the group consisting of H$^3$K8b (comprising SEQ ID NO: 14), H$^3$K8b(+RGD) (comprising SEQ ID NOS: 14 and 15), (-HHHK)H$^3$K8b (comprising SEQ ID NOS: 16 and 17), and (-HHHK)H$^3$K8b(+RGD) (comprising SEQ ID NOS: 16 and 17).

Figure 9:
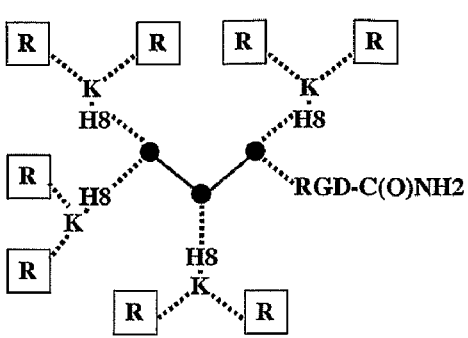
FIG. 9. Important Domains of H³K8b (comprising SEQ ID NO: 14). To determine important domains of H³K8b (comprising SEQ ID NO: 23), several polymers were synthesized that altered one or more of three domains: (+K)H³K8b (comprising SEQ ID NO: 20) adds a single lysine to each of the terminal branches; (-HHHK)H³K8b (comprising SEQ ID NO: 24) removes 4 amino acids from each of the terminal branches; H³K(G)8b (comprising SEQ ID NO: 23) replaces the histidine-rich domain with a glycine; H³K8b(+RGD) (comprising SEQ ID NOS: 14 and 15) has the integrin ligand, RGD.

Transport HK polymers in accordance with the present invention may be synthesized by methods known to those skilled in the art. By way of non-limiting example, certain HK polymers discussed herein may be synthesized as follows. The Biopolymer Core Facility at the University of Maryland may be used to synthesize for example, the following HK polymers on a Ranin Voyager solid-phase synthesizer (PTI, Tucson, Ariz., USA): (1) H$^2$K4b (comprising SEQ ID NO: 21) (83mer; molecular weight 11137 Da); (2) H$^3$K4b (comprising SEQ ID NO: 20) (71mer; MW 9596 Da); (3) HK4b (comprising SEQ ID NO: 22) (79mer; MW 10896 Da); (4) H$^3$K8b (comprising SEQ ID NO: 14) (163mer; MW 23218 Da); (5) H$^3$K8b(+RGD) (comprising SEQ ID NOS: 14 and 15) (166mer; MW 23564 Da); (6) (-HHHK)H$^3$K8b (comprising SEQ ID NOS: 16 and 17) (131mer; MW 18901 Da); (7) (-HHHK)H$^3$K8b(+RGD) (comprising SEQ ID NOS: 16 and 17) (134mer; MW 19243 Da); (8) ((K+) H$^3$K8b(+RGD) (174mer; MW 24594 Da). The structures of certain branched polymers are shown in FIGS. 1 and 9. The polymers with four branches (e.g. H$^3$K4b (comprising SEQ ID NO: 20), HK4b (comprising SEQ ID NO: 22)) may be synthesized by methods known in the art. The sequence of synthesis for highly branched polymers with eight terminal branches may be as follows: (1) RGD or other ligand (if present); (2) the 3-lysine core; (3) histidine-rich domain; (4) addition of a lysine; and (5) terminal branches. The RGD sequence may be initially synthesized by the instrument followed by three manual couplings with (fmoc)-Lys-(Dde)(the lysine core). The (Dde) protecting groups may be removed during the automatic deprotection cycle. To the lysine core, activated amino acids that comprise the histidine-rich domain may then be added sequentially by the instrument. A (fmoc)-Lys-(fmoc) amino acid was added to the histidine-rich domain and the fmoc protecting groups were then removed. To the α and ε amine groups of this lysine, activated amino acids of the terminal branches may then be added. The peptide is cleaved from the resin and precipitated by methods known in the art.

By way of non-limiting example, polymers of the invention may be analyzed as follows. Polymers may be first analyzed by high-performance liquid chromatography (HPLC; Beckman, Fullerton, Calif., USA) and might not be further purified if HPLC reveals that the purity of polymers is 95% or greater. The polymers may be purified on an HPLC column, for example with System Gold operating software, using a Dynamax 21-4×250 mm C-18 reversed phase preparative column with a binary solvent system. Detection may be at 214 nm. Further analyses of the polymers may be performed for example, using a Voyager matrix-assisted laser desorption-ionization time-of-flight (MALDI-TOF) mass spectrometer (Applied Biosystems, Foster City, Calif., USA) and amino acid analysis (AAA Laboratory Service, Boring, Oreg., USA). Transfection agents such as, SuperFect (Qiagen, Valencia, Calif.), Oligofectamine (Invitrogen, Carlsbad, Calif.), Lipofectamine 2000 (Invitrogen), and Lipofectamine (Invitrogen) may be used according to the manufacturers' instructions. DOTAP liposomes may be prepared by methods known in the art.

The present invention is further directed to compositions, which include transfection complexes of the present invention. Such compositions may include for example, one or more intracellular delivery components in association with the HK polymer and/or the siRNA. The intracellular delivery component may include for example, a lipid (such as cationic lipids), a transition metal or other components that would be apparent to those skilled in the art.

In certain embodiments, the composition of the present invention includes a suitable carrier, such as a pharmaceutically acceptable carrier. In these embodiments, there may or may not be a viral or liposomal component. In these embodiments, the complex formed by the transport polymer and the siRNA may be stable at a pH between about 5.0 and 7.4.

In certain embodiments, transfection complex compositions include a transport polymer (which may act as an intracellular delivery component) and siRNA. In these embodiments the transport polymer may act as the intracellular delivery component without need for additional delivery components, or may act in conjunction with other delivery components.

In other embodiments, the transfection complex compositions may include (i) the transport polymer, (ii) at least one intracellular delivery component in association with the transport polymer, and (iii) siRNA in association with the intracellular delivery component and/or the transport polymer. Methods of making these compositions may include combining (i) and (ii) for a time sufficient for the transport polymer and the siRNA to associate into a stable complex. Components (i), (ii) and (iii) may also be provided in a suitable carrier, such as a pharmaceutically acceptable carrier. In embodiments that include an intracellular delivery component other than the transport polymer, the transport polymer may interact with an intracellular delivery component, such as a liposome, through non-covalent or covalent interactions.

The transport polymer may interact with siRNA through non-covalent or covalent interactions. Alternatively, the transport polymer need not interact directly with the siRNA, but rather, the transport polymer may react with an intracellular delivery component(s), which in turn interacts with the siRNA, in the context of the overall complex.

Intracellular delivery components of the present invention can be the transport polymer itself. Where intracellular delivery components other than the transport polymer are utilized such delivery components may be viral or non-viral components. Suitable viral intracellular delivery components include, but are not limited to, retroviruses (e.g., murine leukemia virus, avian, lentivirus), adenoviruses and adeno-associated viruses, herpes simplex viruses, rhinovirus, Sendai virus, and Poxviruses. Suitable non-viral intracellular delivery components include, but are not limited to, lipids and various lipid-based substances, such as liposomes and micelles, as well as various polymers known in the art.

Suitable lipids include, but are not limited to, phosphoglycerides, sphingolipids, phosphatidylcholine, phosphatidylethanolamine, phosphatidylserine, phosphatidylinositol, phosphatidic acid, palmitoyloleoyl phosphatidyleholine, lysophosphatidylcholine, lysophosphatidylethanolamine, dipalmitoylphosphatidylcholine, dioleoylphosphatidylcholine, distearoylphosphatidylcholine, dilinoleoylphosphatidylcholine, glycosphingolipid, amphipathic lipids. The lipids may be in the form of unilamellar or multilamellar liposomes.

The intracellular delivery component may include, but are not limited to, a cationic lipid. Many such cationic lipids are known in the art. A variety of cationic lipids have been made in which a diacylglycerol or cholesterol hydrophobic moiety is linked to a cationic headgroup by metabolically degradable ester bond, for example: 1,2-Bis(oleoyloxy)-3-(4'-trimethylammonio)propane (DOTAP), 1,2-dioleoyl-3-(4'-trimethylammonio)butanoyl-sn-glycerol (DOTB), 1,2-dioleoyl-3- succinyl-sn-glycerol choline ester (DOSC) and cholesteryl (4'-trimethylammonio)butanoate (ChoTB). Other suitable lipids include, but are not limited to, cationic, non-pH sensitive lipids, such as: 1,2-dioleoyl-3-dimethyl-hydroxyethyl ammonium bromide (DORI), 1,2-dioleyloxypropyl-3-dimethyl-hydroxyethyl ammonium bromide (DORIE), and 1,2-dimyristyloxypropyl-3-dimethyl-hydroxyethyl ammonium bromide (DMRIE). Other non-pH-sensitive, cationic lipids include, but are not limited to,: O,O'-didodecyl-N-[p-(2-trimethylammonioethyloxy)benzoyl]-N,N,N-trimethylammonium chloride, Lipospermine, DC-Chol (3 beta [N-(N',N''-dimethylaminoethane) carbonyl]cholesterol), lipopoly(L-lysine), cationic multilamellar liposomes containing N-(alpha-trimethylamnmonioacetyl)-didodecyl-D-glutamate chloride (TMAG), TransfectACE™ (1:2.5 (w:w) ratio of DDAB which is dimethyl dioctadecylammonium bromide and DOPE) (Invitrogen) and lipofectAMINE™ (3:1 (w:w) ratio of DOSPA which is 2,3-dioleyloxy-N-[20([2,5-bis[(3-amino-propyl)amino]-1-oxypentyl]amino)ethyl]-N,N-dimethyl-2,3-bis(9-octadecenylo-xy)-1-propanaminium trifluoroacetate and DOPE) (Invitrogen). Other suitable lipids are described in U.S. Pat. No. 5,965,434, for "Amphipathic PH sensitive compounds and delivery systems for delivering biologically active compounds," by Wolff et al.

Cationic lipids that may be used in accordance with the present invention include, but are not limited to, those that form liposomes in a physiologically compatible environment. Suitable cationic lipids include, but are not limited to cationic lipids selected from the group consisting of 1,2-dioleythyloxypropyl-3-trimethyl ammonium bromide; 1,2-dimyristyloxypropyl-3-dimethyl-hydroxyethyl ammonium bromide; dimethyldioctadecyl ammonium bromide; 1,2-dioleoyl-3-(trimethylammonium)propane (DOTAP); 3.beta.N-(N',N'-dimethylaminoethane)carbamoyl]cholestero-1 (DC-cholesterol); 1,2 dioleolyl-sn-glycero-3-ethylphosphocholine; 1,2 dimyristoly-sn-glycero-3-ethylphosphocholine; [1-(2,3-diol-eyloxy)propyl]-N,N,N-trimethyl-ammonium chloride (DOTMA); 1,3-dioleoyloxy-2-(6carhoxys-permyl) propylamide (DOSPER); 2,3-dioleyloxy-N-[2(spermine-carboxyamido)et-hyl]-N,N, dimethyl-1-propanamoniumtrifluoroacetate (DOSPA); and 1,2-dimyristyloxypropyl-3-dimethyl-hydroxyethyl ammonium bromide (DMRIE).

Cationic lipids may be used with one or more helper lipids such as diloleoylphosphatidylethanolamine (DOPE) or cholesterol to enhance transfection. The molar percentages of these helper lipids in cationic liposomes are between about 5 and 50%. In addition, pegylated lipids, which can prolong the in vivo half-life of cationic liposomes, can be present in molar percentages of between about 0.05 and 0.5%.

Compositions in accordance with the present invention may alternatively include one or more components to enhance transfection, to preserve reagents, or to enhance stability of the delivery complex. For example, stabilizing compounds such as polyethylene glycol can be covalently attached to either the lipids or to the transport polymer.

Compositions in accordance with the present invention may include a suitable buffer solution whose pH is between about 4 and 7.4. Preferably within two hours of neutralizing acidic solutions to between a pH of about 5.0 and 7.4, the composition is administered. The various components of the composition may be lyophilized and reconstituted with a buffer with a pH of between about 5.0 and 7.4. Stability and solubility of the polymer, particularly when complexed to large negatively charged macromolecules such as DNA, may be maintained at slightly acidic solutions.

The compositions of the invention may include a dendrimer. The intracellular delivery component and the siRNA may together comprise a dendrimer-siRNA complex.

Compositions of the present invention may also suitably include various delivery-enhancing components known in the art. For example, the composition may include one or more compounds known to enter the nucleus or ligands subject to receptor-mediated endocytosis, and the like. For example, the ligand may comprise a fusogenic viral peptide to disrupt endosomes, allowing the nucleic acid to avoid lysosomal degradation. Other examples of delivery-enhancing components include, but are not limited to, nuclear proteins, adenoviral particles, transferrin, surfactant-B, anti-thrombomodulin, intercalating agents, hemagglutinin, asialglycoprotein, chloroquine, colchicine, integrin ligands, LDL receptor ligands, and viral proteins to maintain expression (e.g. integrase, LTR elements, rep proteins, oriP and EBNA-1 proteins) or viral components that interact with the cell surface proteins (e.g. ICAM, HA-1, MLV's gp70-phosphate transporter, and HIV's gp120-CD4). Delivery enhancing components can be covalently or non-covalently associated with the transport polymer, the intracellular delivery component, or the pharmaceutical agent. For instance, delivery to a tumor vasculature can be targeted by covalently attaching a -RGD- or -NGR- motif. This could be accomplished using a peptide synthesizer or by coupling to amino groups or carboxyl groups on the transport polymer with a water-soluble di-carbodiimide (e.g., 1-ethyl-3-(3-dimethyaminopropyl)carboiimide). Both of these methods are known to those familiar with the art.

Compositions of the present invention may suitably include a transition metal ion, such as a zinc ion. The presence of a transition metal in the complexes of the invention may enhance transfection efficiency.

The present invention further includes assays for determining an effective carrier of siRNA for transfection into cells. These assays include mixing siRNA with a transport polymer to form a transfection complex; contacting the transfection complex with one or more cells; and detecting the presence or absence of siRNA activity within the cells. In certain embodiments, the siRNA is directed toward β-galactosidase.

The present invention also provides methods of treating diseases comprising using the complexes or compositions of the present invention. In particular, methods are provided for treating a patient having a disease, by administering to the patient a therapeutically effective amount of a complex or composition of the present invention. Also encompassed are methods for treating a patient having a disease, by administering to the patient cells that have been transfected by the methods disclosed herein. Examples of genetic and/or non-neoplastic diseases potentially treatable with the complex, compositions, and methods include, but are not limited to the following: adenosine deaminase deficiency; purine nucleoside phosphorylase deficiency; chronic granulomatous disease with defective p47phox; sickle cell with HbS, β-thalassemia; Faconi's anemia; familial hypercholesterolemia; phenylketonuria; ornithine transcarbamylase deficiency; apolipoprotein E deficiency; hemophilia A and B; muscular dystrophy; cystic fibrosis; Parkinsons, retinitis pigmentosa, lysosomal storage disease (e.g., mucopolysaccharide type 1, Hunter, Hurler and Gaucher), diabetic retinopathy, human immunodeficiency virus disease virus infection, acquired anemia, cardiac and peripheral vascular disease, and arthritis. In some of these examples of diseases, the therapeutic gene may encode a replacement enzyme or protein of the genetic or acquired disease, an antisense or ribozyme molecule, a decoy molecule, or a suicide gene product.

Ex vivo and in vivo gene therapy with siRNA could also be used in cancer. These siRNA applications toward cancer include, but are not limited to, 1) reducing expression of growth factors, reducing proteins that augment the cell cycle (e.g., Raf-1, PI-3 kinase), growth factor receptors (e.g., EGFR, Her-2), or proteins critical for supporting cells of the tumor (e.g., VEGF, VEGFR1-2 for tumor endothelial cells); 2) targeting or reducing expression of factors that are anti-apoptotic (e.g., BCL-2); and 3) targeting proteins or enzymes that reduce immune activation toward tumor.

The present invention also provides a method of ex vivo gene therapy comprising: (i) removing a cell from a subject; (ii) delivering a nucleic acid (such as siRNA) to the interior of the cell by contacting the cell with a transfection complex or composition comprising such a transfection complex of the present invention; and (iii) administering the cell comprising the nucleic acid (e.g., siRNA) to the subject.

Recombinant cells may be produced using the complexes of the present invention. Resulting recombinant cells can be delivered to a subject by various methods known in the art. In certain embodiments, the recombinant cells are injected, e.g., subcutaneously. In other embodiments, recombinant skin cells may be applied as a skin graft onto a patient Recombinant blood cells (e.g., hematopoietic stem or progenitor cells) are preferably administered intravenously. The cells can also be encapsulated in a suitable vehicle and then implanted in the subject (see, e.g., Dionne et al. PCT Publication WO92/19195, dated Nov. 12, 1992). The amount of cells administered depends on a variety of factors known in the art, for example, the desired effect, subject state, rate of expression of the chimeric polypeptides, etc., and can readily be determined by one skilled in the art.

The following examples illustrate specific embodiments of the invention. The examples set forth herein are meant to be illustrative and should not in any way serve to limit the scope of the claimed invention. As would be apparent to skilled artisans, various changes and modifications are possible and are contemplated within the scope of the invention described, and may be made by persons skilled in the art without departure from the spirit of the invention.

EXAMPLES

Example 1

Methods

Several branched polymers were synthesized on a Ranin Voyager synthesizer (PTI, Tucson, Ariz.) by methods known to those skilled in the art. These polymers were then screened for their ability to transfer siRNA into SVR-bag4 cells, MDA-MB-435 cells, and C6 cells. After one polymer, H$^3$K8b (comprising SEQ ID NO: 14), was identified as an effective carrier of siRNA and investigated with flow cytometry for toxicity, additional polymers were synthesized to determine important domains for siRNA transport. The size/zeta potential of HK:siRNA complexes was then calculated with the N4 Submicron Particle Size Analyzer and the Delsa 440 SX Zeta Potential Analyzer, respectively.

Cell lines: MDA-MB-435 (a malignant breast cancer cell line), C6 (rat glioma cell line), C6/lacZ (C6 line that expresses β-galactosidase) and SVR-bag4 (a mouse endothelial cell line, transformed by SV virus, that expresses β-galactosidase), were maintained in Dulbecco's Minimal Essential Medium (DMEM) containing about 10% fetal calf serum and about 20 mM glutamine.

Transfection agents: HK Polymers and other carriers: The biopolymer core facility at the University of Maryland synthesized HK polymers on a Ranin Voyager synthesizer (PTI, Tucson, Ariz.). The structures of the branched polymers are shown in FIGS. 1 and in 9. The polymers were then purified using HPLC. The transfection agents, Superfect (Qiagen), Oligofectamine (Invitrogen) and Lipofectamine (Invitrogen), were used according the manufacturer's instructions. DOTAP was prepared as described herein.

siRNA: The siRNA duplexes with their target in parentheses are as follows: 1) luciferase siRNA, sense 5'-CUU ACG CUG AGU ACU UCG A dTdT-3' (SEQ ID NO: 2) and antisense, 5'-U CGA AGU ACU CAG CCU AAG dTdT-3' (SEQ ID NO: 3) (target 5'-CTT ACG CTG AGT ACT TCG-3' (SEQ ID NO: 4)); and 2) β-galactosidase (β-gal) siRNA, sense 5'-CAG UUG CGC AGC CUG AAU G dTdT-3' (SEQ ID NO: 5) and antisense, 5'-CAG UUG CGC AGC CUG AAT G dTdT-3' (SEQ ID NO: 6) (target 5'-AAC AGU UGC GCA GCC UGA AUG-3' (SEQ ID NO: 7)). For siRNA import studies, Cy3-labeled siRNA (sense, 5'-CGU ACG CGG AAU ACU UCG A-dTdT-3' (SEQ ID NO: 8) and antisense, 5'-T CGA AGU AUU CCG CGU ACG-dTdT-3' (SEQ ID NO: 9)) was purchased from Darmacon.

siRNA Transfection: Initially, 3×10$^4$ SVR-bag4 cells were plated into a 24-well plate containing about 500 µl per well of DMEM with 10% serum. After about 24 h, when the cells were about 40% confluent, transfection complexes were added to the media. To prepare complexes of the carrier: siRNA (ratio of 4:1 unless otherwise indicated), siRNA (2 µg) in OptiMEM was briefly mixed well with the carrier (about 8 µg) and allowed to stand at room temperature for about 30 min. The total volume of the polymer/DNA complex in OptiMEM was about 50 µl and this complex was added drop wise to the cells in about 0.5 ml of DMEM/10% serum.

For Lipofectamine 2000, the transfection method was similar except that the carrier:siRNA ratio was 2:1; in addition, the Oligofectamine:siRNA ratio was 2:1 and the complex was added to cells in 0.5 ml DMEM for 4 h before media was changed to DMEM/10% FCS.

β-Galactosidase staining and activity assays. About forty-eight hours after β-gal siRNA transfection of SVR-bag4 cells, the intracellular level of β-galactosidase was determined by using β-galactosidase staining and assay kits (Invitrogen) as described by the manufacturer. The growth medium was removed from the transfected cells, which were then washed with PBS. For staining, the cells were fixed for about 10 min at room temperature and washed twice with PBS; X-gal staining solution was added to the cells and incubated at about 37° C. for about 6 h. To determine β-galactosidase activity, lysis buffer (about 50 ml) was added to each well, and the cells were freezed-thawed for three cycles. The β-galactosidase substrate, ONPG, was then incubated with the cells at 37° C. for 30 min. The reaction was stopped with 1 M sodium carbonate solution and the absorbance at 420 nm was read. β-galactosidase specific activity was reported as nmoles of ONPG hydrolyzed/min/mg of protein lysate.

Co-transfection with a luciferase expression plasmid and luciferase-targeting siRNA. About twenty-four hours after about 1×10$^5$ MDA-MB-435 cells were plated in a 24 well plate to reach about 70% confluency, these cells were co-transfected with a plasmid and siRNA. The luciferase expression plasmid (Promega, Madison, Wi) in complex with SuperFect (2:1), and the siRNA (targeting luciferase mRNA) in complex with one of several carriers were prepared separately at the same time. These two complexes were then added together to the cells; about 24 h later, the cells were washed with PBS and subsequently lysed with about 100 µl of 1×passive lysis buffer (Promega Corp). Protein concentration was measured by using the BCA protein assay kit (Pierce). Luciferase activity was measured with the direct current Turner 20/20 luminometer (Turner Design, Sunnyvale, Calif.). Relative light units were converted to picograms (pg) of luciferase by using recombinant luciferase (Promega, Madison, Wis.) as a standard. Duplicate measurements were made at each concentration and three separate experiments were conducted.

Results

In an endothelial cell line (SVR-bag4) that stably expressed β-galactosidase, an siRNA in complex with the H$^3$K8b (comprising SEQ ID NO: 14) polymer inhibited β-galactosidase expression by greater than 80%. Similarly, H$^3$K8b (comprising SEQ ID NO: 14) in complex with a luciferase-targeting siRNA inhibited luciferase expression in MDA-MB-435 cells. In contrast, the polymer, H$^2$K4b (comprising SEQ ID NO: 21), which was an effective carrier of plasmids, was not an efficient carrier of siRNA. At an optimal concentration for inhibiting its target, the H$^3$K8b:siRNA complex had minimal toxicity. The histidine-rich domain and the length of the terminal arms of H$^3$K8b (comprising SEQ ID NO: 14) seemed to affect siRNA delivery. The size and surface charge, however, did not appear to affect delivery siRNA.

Conclusions

Thus, both the degree of complexity and the sequence specificity are factors to be considered for developing the HK carrier of siRNA. In particular, the inventor found that certain branched HK polymers (H$^3$K8b (comprising SEQ ID NO: 14) and similar structural analogs) with eight terminal branches and a histidine-rich domain were effective carriers of siRNA.

Example 2

Uptake Experiments

Cells were transfected as described above with carriers (DOTAP, Lipofectamine, or H$^2$K4b (comprising SEQ ID NO: 21), or H$^3$K8b (comprising SEQ ID NO: 14)) in complex with Cy3-labeled siRNA; about 4 h later, images were obtained with a Diaphot-TMD fluorescence microscope, 100×(Nikon, Tokyo, Japan).

Flow cytometry. To determine cellular toxicity after transfection with the H$^3$K8b: siRNA complex, the manufacturers' instructions for the Vybrant Apoptosis Assay #4 (Molecular Probes) were followed. Twenty-four hours prior to transfection, 2×10$^5$ SVR-bag4 cells were plated in each well of a 12-well plate. The cells were transfected with a β-galactosidase-expressing siRNA (about 2 μg) in complex with the carrier (H$^3$K8b (comprising SEQ ID NO: 14), DOTAP, Lipofectamine, 8 μg; Oligofectamine, Lipofectamine 2000; 4 μg). The cells were then harvested after about 24 h, washed in cold 1×PBS, and the cells were suspended in about 1 ml of PBS. To this suspension, about 1 μl of the green fluorescent dye stock solution (YO-PRO-1) and about 1 μl of the red fluorescent stock solution (propidium iodide) was added. After incubation on ice for about 30 min, the number of cells that were viable, necrotic, and/or apoptotic was analyzed by the FACScan using 488 nm excitation (Becton Dickinson, San Jose, Calif.). The percentage of nonviable cells was then calculated from the different carrier: siRNA complexes after subtracting the nonviable cells of the untreated group. (See FIGS. 7 and 8).

Figure 8:
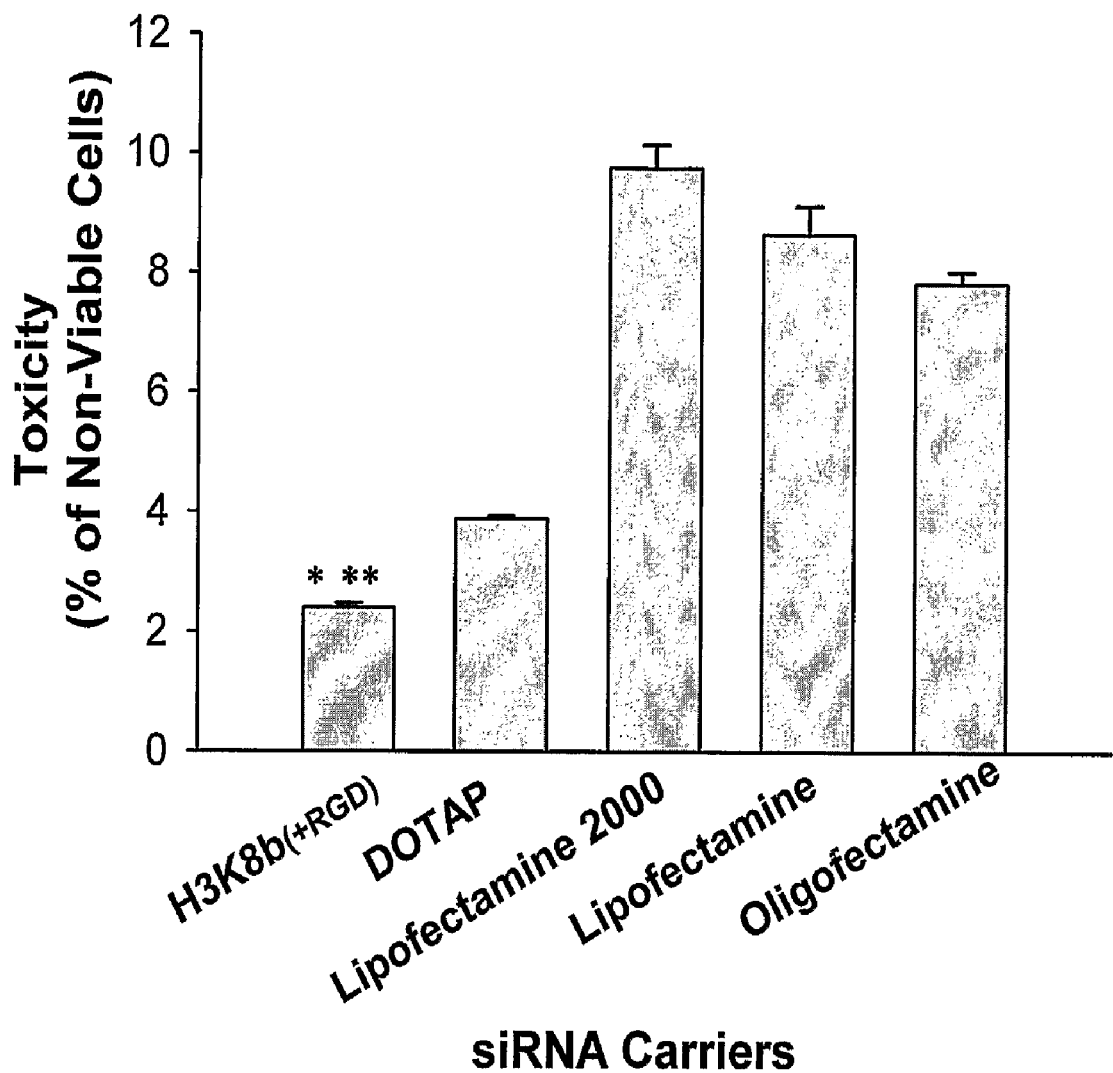
FIG. 8. Toxicity induced by various carrier:siRNA complexes. SVR-bag4 cells were transfected with various carriers in complex with a β-gal siRNA detailed in the examples. The cells were then treated with YO-PRO-1 and PI fluorescence dyes and analyzed by flow cytometry using 488 nm excitation. Toxicity (or non-viable cells) was determined by the percent of cells excluded from viable cell group. Data represent the mean and S.D. of triplicate experiments. *, P<0.05, H³K8b(+RGD) (comprising SEQ ID NOS: 14 and 15) vs DOTAP; **, P<0.001, H³K8b(+RGD) (comprising SEQ ID NOS: 14 and 15) vs Lipofectamine, Lipofectamine 2000, or Oligofectamine (One way anova with Bonferroni multiple comparison tests). The ratio for the transfection carrier: siRNA complexes was 4:1 (wt:wt) except for Lipofectamine 2000 and Oligofectamine complexes in which the ratio was 2:1.

The data depicted in FIG. 8 represent the mean and S.D. of three experiments; **P<0.001, H$^3$K8b(+RGD) (comprising SEQ ID NOS: 14 and 15) vs. Lipofectamine, Lipofectamine 2000, or Olifofectamine (One way ANOVA with Bonferroni multiple comparison tests). The ratio for the transfection carrier:siRNA complexes was 4:1 (w/w) except for Lipofectamine 2000 and Oligofectamine complexes in which the ratio was 2:1.

Measurement of the size and zeta-potential of the DNA-HK polymer complexes HK polymers, H$^3$K8b(−RGD) and H$^2$K4b, (comprising SEQ ID NO: 21) (24 or 48 μg) in complex with plasmid DNA (about 12 μg) were prepared similarly to the transfection complexes described previously. After the polymer complexes (polyplexes) stood in Opti-MEM (about 300 μl) for about 30 minutes, about 950 μl of Hepes buffer (about 20 mM, pH about 7.5) was added to the wells. Particle sizes of various complexes were determined by measuring light scattering at about a 90 degree angle on an N4 Submicron Particle Size Analyzer (Beckman Coulter, Hialeah, Fla.). The particle size is reported as the average size obtained from a Unimodal analysis carried out using the software provided by the instrument manufacturer. Zeta potential, a measure of a particle surface charge, was measured using a Delsa 440 SX instrument (Coulter). Zeta potential values were determined for the mobility of particles in an electric field. Each data point represents the mean+S.D. of three measurements.

Results

Figure 2:
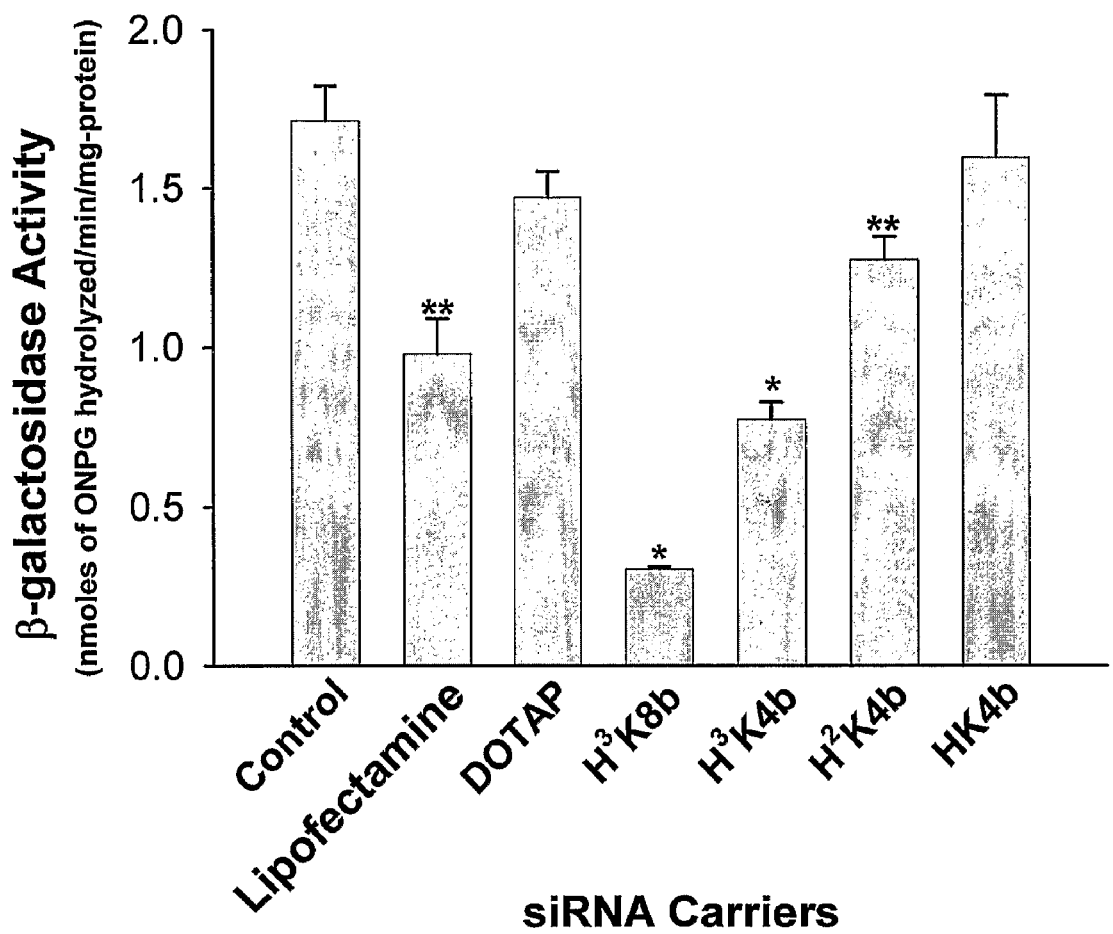
FIG. 2. H³K8b (comprising SEQ ID NO: 14) is an effective carrier of siRNA.
Figure 3:
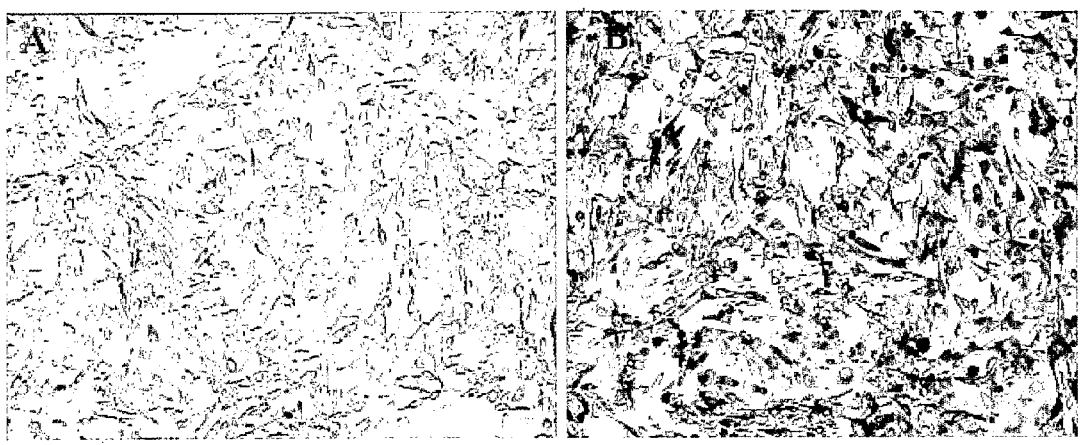
FIG. 3. H³K8b(+RGD) (comprising SEQ ID NOS: 14 and 15) in complex with β-gal siRNA, markedly inhibits β-galactosidase expression. SVR-bag4 cells were transfected with H³K8b(+RGD) (comprising SEQ ID NOS: 14 and 15) in complex with β-gal siRNA (4:1; μg:μg ratio) for 48 h, and β-galactosidase activity was then measured by use of a β-galactosidase staining kit. β-galactosidase staining confirmed that H³K8b(+RGD) (comprising SEQ ID NOS: 14 and 15) in complex with the β-gal siRNA markedly inhibited β-galactosidase activity of SVR-bag4 cells.

H$^3$K8b (comprising SEQ ID NO: 14) is an effective carrier of siRNA. Several branched HK peptides were synthesized and examined as carriers of siRNA into cells. Representatives of these HK peptides tested as siRNA carriers are shown in FIG. 1. In FIG. 2, the efficiency of these HK carriers in the delivery of an siRNA targeting β-galactosidase (β-gal) expressed in SVR-bag4 cells was compared. The carriers with four terminal branches were not particularly effective carriers of siRNA with the modest exception of H$^3$K4b (comprising SEQ ID NO: 20). Notably, peptides such as H$^2$K4b (comprising SEQ ID NO: 21), effective carriers of plasmids, were not successful carriers of siRNA. The H$^3$K8b (comprising SEQ ID NO: 14) polymer, with eight terminal branches, was the most effective carrier of the siRNA in reducing the intracellular target by about 80%. Compared to other HK polymers, it is more highly branched and has the highest percentage of histidines and the lowest percentage of lysines. H$^3$K8b (comprising SEQ ID NO: 14) was about 5-fold less effective for transfection of plasmids compared to H$^2$K4b (comprising SEQ ID NO: 21). β-galactosidase staining confirmed that H$^3$K8b (comprising SEQ ID NO: 14) in complex with the β-gal siRNA markedly inhibited β-galactosidase activity in SVR-bag4 cells (FIG. 3).

Figure 4:
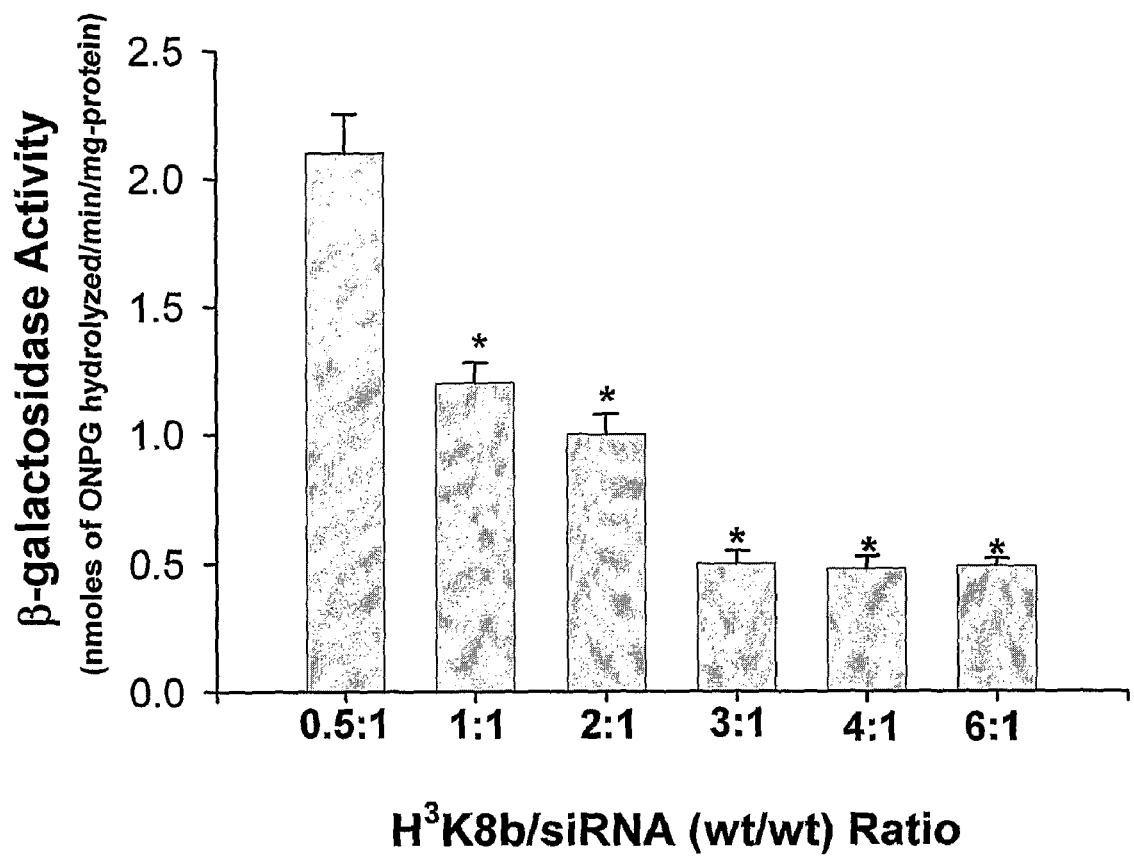
FIG. 4. An optimal H³K8b:siRNA ratio.

H$^3$K8b:siRNA ratios for reducing β-galactosidase expression were also determined. The ratio was varied from about 0.5:1 to about 6:1 (wt:wt), or between about 3:1 and about 6:1 (FIG. 4). A 3:1 wt:wt ratio corresponds to about a 1.7 N(+): P(−) ratio. Next, it was found that β-gal staining of SVR-bag4 cells was markedly inhibited by the H$^3$K8b (+RGD) (comprising SEQ ID NOS: 14 and 15) in complex with the β-gal siRNA. (FIG. 3). In addition in a C6 cell line that stably expresses β-galactosidase, H$^3$K8b (comprising SEQ ID NO: 14) in complex with β-gal siRNA inhibited β-galactosidase expression by about 60%.

Example 3

Figure 5:
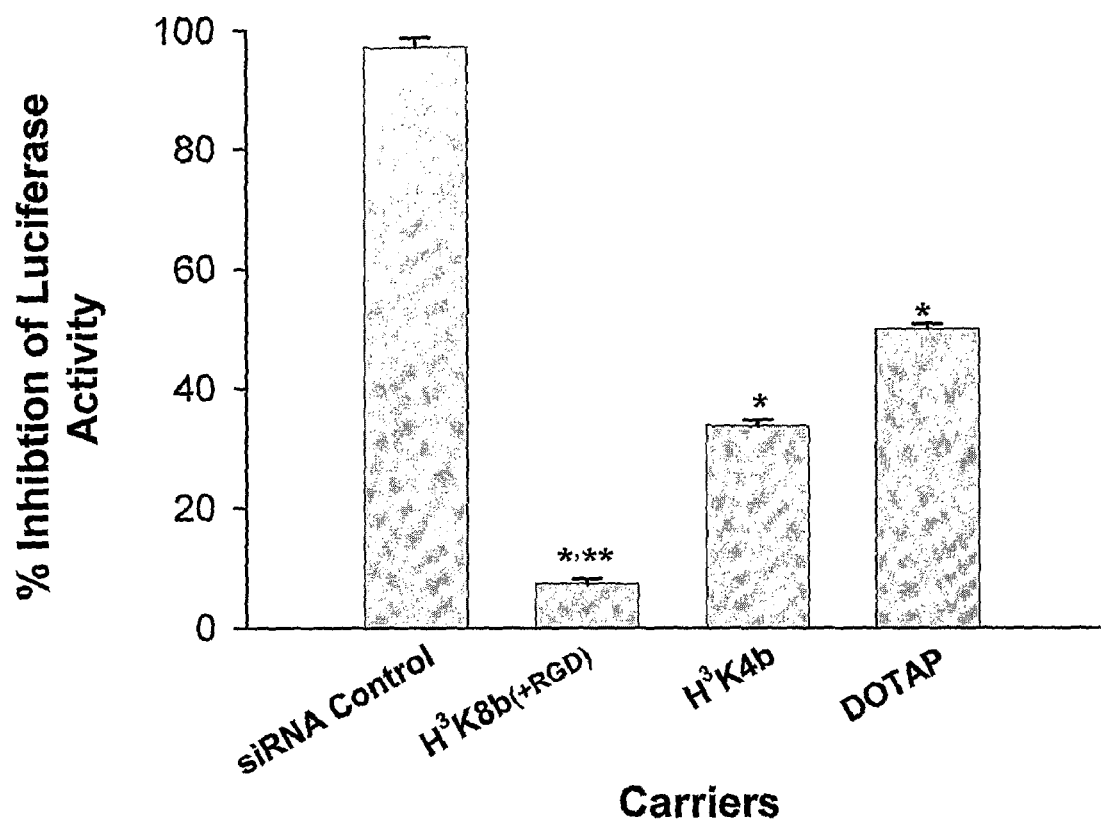
FIG. 5. H³K8b(+RGD) (comprising SEQ ID NOS: 14 and 15) in complex with a luciferase-targeting siRNA markedly inhibits luciferase activity.

Marked inhibition of luciferase activity by H$^3$K8b-mediated luciferase siRNA delivery. The inventor next determined the efficiency of H$^3$K8b(+RGD) (comprising SEQ ID NOS:

14 and 15) in transporting a siRNA targeting transfected luciferase in a malignant cell line, MDA-MB 435 cells (FIG. 5). These cells were co-transfected with a luciferase-expression plasmid in complex with SuperFect together with a luciferase-targeting siRNA in complex with one of these carriers: H³K8b(+RGD) (comprising SEQ ID NOS: 14 and 15), H³K4b (comprising SEQ ID NO: 20), or DOTAP. The results showed that the H³K8b(+RGD):Luc siRNA complex was the most effective, inhibiting about 90% luciferase activity as compared to the H³K8b: β-gal siRNA control. Thus, H³K8b (+RGD) (comprising SEQ ID NOS: 14 and 15) was the most effective carrier of siRNA both in the β-galactosidase-expressing SVR-bag4 cells and in the co-transfection experiments with MDA-MB-435 cells.

Example 4

Figure 6:
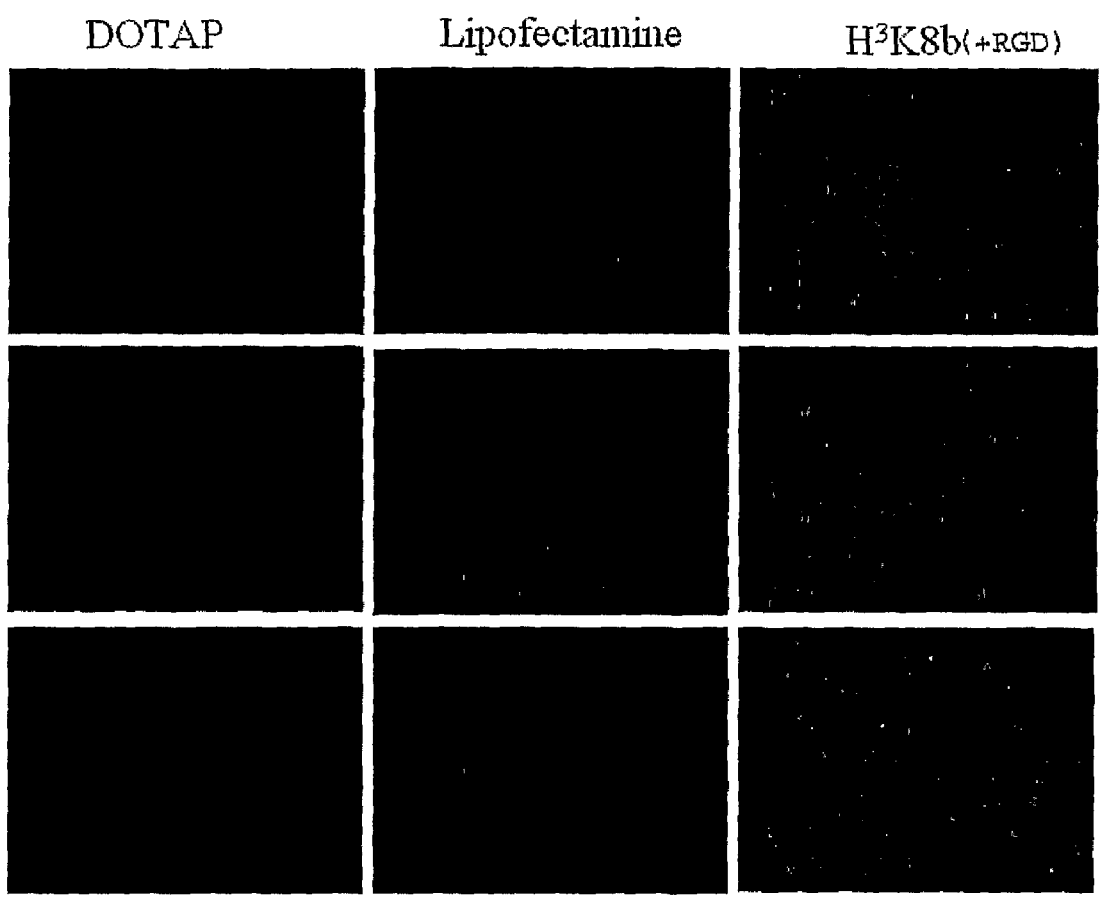
FIG. 6. Comparison of H³K8b(+RGD) (comprising SEQ ID NOS: 14 and 15) and other carriers increased the uptake efficiency of Cy3 labeled siRNA.

H³K8b(+RGD)-mediated siRNA delivery is highly efficient in several cell lines. To determine the mechanism of H³K8b(+RGD) (comprising SEQ ID NOS: 14 and 15) as an effective carrier for siRNA, the uptake of the H³K4b(+RGD): siRNA complex in three cell lines (SVR-bag4, MDA-MB-435 and C6 cells) was examined. These cells were then transfected with Cy3-labeled siRNA in complex with DOTAP (4:1 ratio; carrier (mg)/siRNA (mg) ratio), Lipofectamine (4:1), or H³K8b(+RGD) (comprising SEQ ID NOS: 14 and 15) (4:1). As shown in FIG. 6, siRNA fluorescence with the H³K8b(+RGD) (comprising SEQ ID NOS: 14 and 15) carrier was much greater than with the DOTAP and Lipofectamine groups. In addition, siRNA fluorescence transported intracellularly by H³K8b(+RGD) (comprising SEQ ID NOS: 14 and 15) was greater than other HK carriers including H²K4b (comprising SEQ ID NO: 21) and HK4b (comprising SEQ ID NO: 22) (data not shown). In the three cell lines, the Cy3-labeled siRNA delivered by H³K8b (comprising SEQ ID NO: 14) showed discrete foci of fluorescence and perinuclear distribution. The uptake of the siRNA by the HK carriers correlates with the desired effect.

Figure 7:
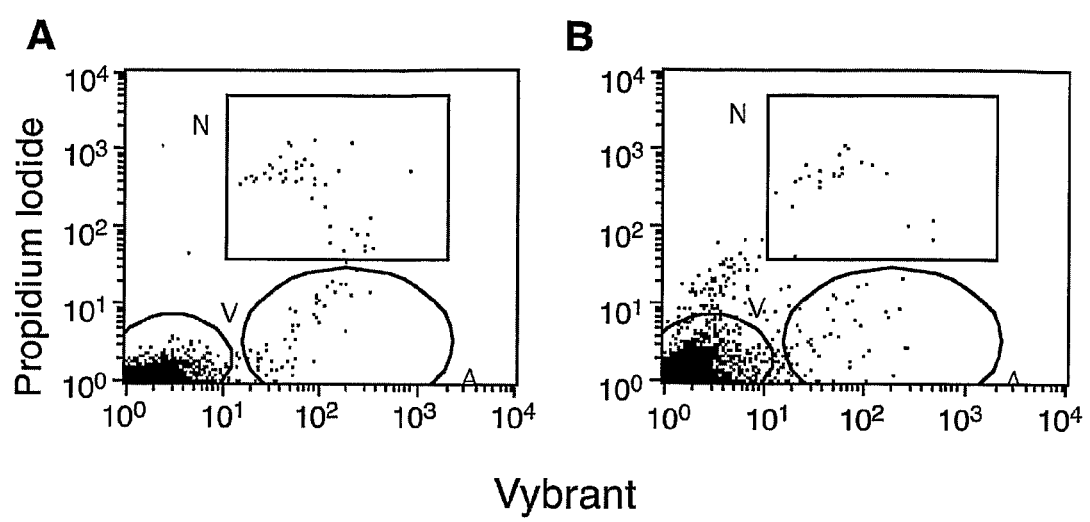
FIG. 7 Apoptosis and Necrosis induced by H³K8b:siRNA complex. SVR-bag4 cells were transfected with H³K8b (comprising SEQ ID NO: 14) in complex with a β-gal siRNA as detailed in the Examples below. The treatment groups were untreated (A) and H³K8b:siRNA complex (4:1 ratio; wt/wt) (B). The cells were then treated with YO-PRO-1 and PI fluorescence dyes and analyzed by flow cytometry using 488 nm excitation. V: viable cells; A: apoptotic cells; N: necrotic cells.

Minimal toxicity observed with H³K8b(+RGD):siRNA complexes After staining the transfected SVR-bag4 cell population with the YO-PRO-1 and PI dyes, apoptotic cells showed green fluorescence, dead cells showed red and green fluorescence, and the viable cells showed little or no fluorescence. H³K8b(+RGD) (comprising SEQ ID NOS: 14 and 15) in complex with β-gal siRNA (H³K8b(+RGD):siRNA; 4:1 wt/wt ratio) showed minimal toxicity compared to the untreated cells (FIG. 7) with minimal apoptosis and/or cell death. Other carriers of siRNA including Oligofectamine and Lipofectamine 2000, were significantly more toxic to cells. (FIG. 7). In duplicate transfection experiments, the cell populations were classified into viable (V), apoptotic (A), and necrotic (N) groups. For untreated cells, the proportion of viable, apoptotic, and necrotic cells was 95.79, 1.65, and 1.75, respectively; for the H³K8b: siRNA complex, the proportion of viable, apoptotic, and necrotic cells was 91.99, 2.22, and 1.39, respectively. Thus, apoptosis and/or cell death from the HK: siRNA complex was less than about 5%. Data represents the mean of triplicate experiments.

Example 5

Domains of H³K8b (comprising SEQ ID NO: 14). In certain embodiments the inventor developed several domains in H³K8b (comprising SEQ ID NO: 14) which aide in the transport of siRNA: 1) the terminal branches (e.g., HHHKHHH-KHHHKHHH, SEQ ID NO: 18), which likely bind to siRNA, 2) the histidine rich core (H8), and 3) the integrin-binding domain. Addition of an integrin-binding ligand (+RGD) to H³K8b (comprising SEQ ID NO: 14) may augment the transport and efficacy of siRNA. To investigate these potentially important regions for siRNA import, the inventor synthesized several HK polymers in which the domains of H³K8b (comprising SEQ ID NO: 14) were altered (see e.g., FIG. 9). The addition of RGD to H³K8b (comprising SEQ ID NO: 14) (e.g., H³K8b(+RGD) (comprising SEQ ID NOS: 14 and 15)) slightly increased the efficacy of the siRNA in SVR-bag4 cells (FIG. 10) and in MDA-MB-435 cells, a 20% enhancement in siRNA efficacy was observed with H³K8b(+RGD) (comprising SEQ ID NOS: 14 and 15) compared to H³K8b (comprising SEQ ID NO: 14) as a siRNA carrier. When several amino acids were removed from the terminal branch of H³K8b (comprising SEQ ID NO: 14) or H³K8b(+RGD) (comprising SEQ ID NOS: 14 and 15), the efficacy of the transport polymer of siRNA was reduced minimally (approximately 25%). Thus, there is tolerance in shortening the length of the terminal branches of H³K8b (comprising SEQ ID NO: 14) that carry siRNA.

When one lysine was added to each of the terminal branches (eight additional lysines per polymer), the efficacy of the branched HK polymer as a siRNA carrier is reduced significantly.

In another embodiment the H8 domain was replaced with a glycine, and the result showed decreased efficacy of siRNA by about 3-fold.

An optimal ratio of H³K8b:siRNA complex (wt:wt) was between about 2:1 and about 4:1. Notably, H³K8b (comprising SEQ ID NO: 14) was better than Oligofectamine as a carrier of siRNA into SVR-bag4 cells.

Example 6

Size and Zeta Potential of HK: siRNA Complexes. The inventor next compared the size and zeta potential of H³K8b (comprising SEQ ID NO: 14) and H²K4b (comprising SEQ ID NO: 21) in complex with β-gal siRNA. While H³K8b (comprising SEQ ID NO: 14) was an effective carrier for siRNA, H²K4b (comprising SEQ ID NO: 21) was not an effective carrier for siRNA. Notably, both H³K8b (comprising SEQ ID NO: 14) and H²K4b (comprising SEQ ID NO: 21) polymers lacked the integrin ligand, RGD. As seen in Table 1, the size of H³K8b (comprising SEQ ID NO: 14) complex was modestly smaller than the H²K4b (comprising SEQ ID NO: 21) complex.

TABLE 1

Size and Zeta-Potential of HK Polyplexes

| | Size (nm) | | Zeta Potential (mV) | |
| --- | --- | --- | --- | --- |
| | H²K4b (comprising SEQ ID NO: 21) | H³K8b (comprising SEQ ID NO: 14) | H²K4b (comprising SEQ ID NO: 21) | H³K8b (comprising SEQ ID NO: 14) |
| 2:1 | 916 ± 34 | 412 ± 57 | 12.8 ± 1.4 | −6.9 ± 0.3 |
| 4:1 | 875 ± 32 | 509 ± 81 | 17.7 ± 1.2 | 8.2 ± 1.4 |

HK polymers (48 µg or 96 µg) in complex with plasmid DNA (12 µg) were prepared similarly in Opti-MEM (300 µl) as the transfection complexes. After the polyplexes stood for 30 minutes, about 950 µl of Hepes buffer (pH 7.5, 20 mM) was added. The size and surface charge were measured with the N4 Plus Submicron Particle Size Analyzer and the Delsa 440 SX Zeta Potential Analyzer, respectively. Each data point represents the mean of three measurements.

With a greater histidine:lysine ratio in which the histidines have little charge at physiological pH, the zeta potential for the H$^3$K8b:siRNA complexes was reduced compared to H$^2$K4b:siRNA complexes. While the zeta potential of the H$^3$K8b:siRNA, prepared at a 2:1 ratio, and H$^2$K4b:siRNA complexes, prepared at a 4:1 ratio, were similar, their ability to transport siRNA differed markedly. Furthermore, while the zeta potential changed from positive to negative by varying H$^3$K8b:siRNA ratio, inhibition of lacZ mRNA by these complexes with different charges were similar. Ratios between 2:1 and 6:1 (w/w) were best for the H$^3$K8b (comprising SEQ ID NO: 14) polymer:β-gal siRNA complex and inhibited intracellular β-gal levels similarly.

Example 7

Several polymers were synthesized that altered one or more of the domains of H$^3$K8b (comprising SEQ ID NO: 14), H$^3$K8b(+RGD) (comprising SEQ ID NOS: 14 and 15) adds the integrin ligand RGD; (+K)H$^3$K8b(+RGD) (comprising SEQ ID NO: 20) adds a single lysine to each of the terminal branches; H$^3$K(G)8b(+RGD) has replaced the histidine-rich domain with a single glycine (represented by G); (-HHHK) H$^3$K8b (comprising SEQ ID NOS: 16 and 17) or (-HHHK) H$^3$K8b(+RGD) (comprising SEQ ID NOS: 16 and 17) removes for amino acids from each of the terminal branches. Schematic drawings of these modifications of H$^3$K8b (comprising SEQ ID NO: 14) are depicted in FIG. 9. The three solid circles connected by a solid line represent the three-lysine core and the K represents the lysine in which the two terminal branches are conjugated.

The effective analog of H$^3$K8b (comprising SEQ ID NO: 14) containing an integrin ligand, H$^3$K8b(+RGD) (comprising SEQ ID NOS: 14 and 15), was able to inhibit markedly intracellular β-gal expression. Furthermore, it was determined that H$^3$K8b(+RGD) (comprising SEQ ID NOS: 14 and 15) in complex with luciferase-targeting siRNA inhibited luciferase expression in MDA-MB-435 cells. At an optimal concentration for inhibiting its target, H$^3$K8b(+RGD):siRNA complex has minimal toxicity. In contrast, carriers of siRNA such as Oligofectamine and Lipofectamine 2000 were significantly more toxic.

The addition of a single lysine to the terminal branches in (+K)H$^3$K8b(+RGD) (comprising SEQ ID NO: 20) or the replacement of the histidine-rich domain (H8) with a glycine in H$^3$K(G)8b(+RGD) significantly reduced the ability of these polymers as carriers of siRNA.

Figure 10:
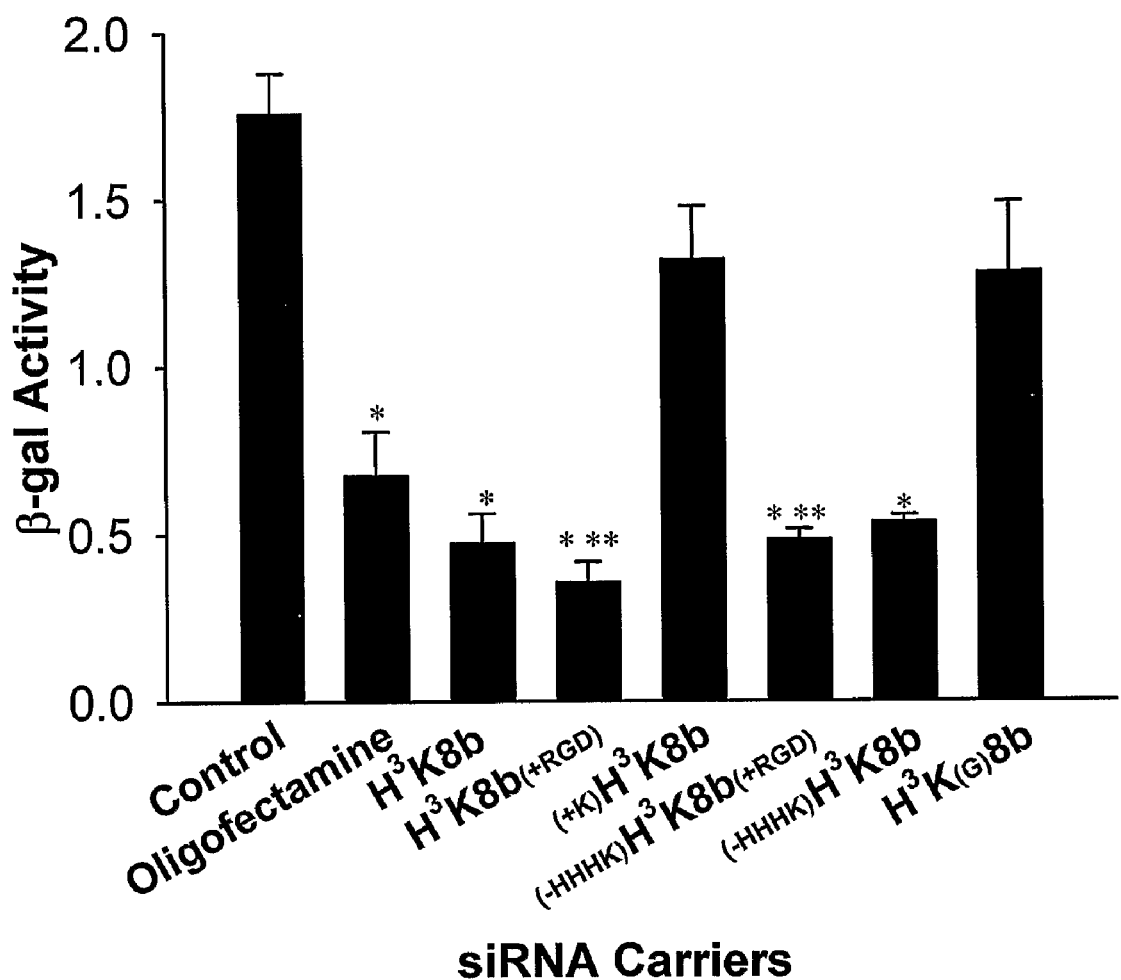
FIG. 10.

The data depicted in FIG. 10 represent the mean±S.D. of three experiments; P<0.01: untreated vs. Oligofectamine, H$^3$K8b (comprising SEQ ID NO: 14), (-HHHK)H$^3$K8b (comprising SEQ ID NOS: 16 and 17), H$^3$K8b(+RGD) (comprising SEQ ID NOS: 14 and 15), and (-HHHK)H$^3$K8b(+RGD) (comprising SEQ ID NOS: 16 and 17), P<0.01, Oligofectamine vs. H$^3$K8b(+RGD) (comprising SEQ ID NOS: 14 and 15) or (-HHHK)H$^3$K8b(+RGD) (comprising SEQ ID NOS: 16 and 17) (One way ANOVA with Bonferroni multiple comparison tests). The ratio of HK polymers and Oligofectamine in complex with siRNA was 4:1 and 2:1 (w/w), respectively.

As shown in FIG. 10, H$^3$K8b(+RGD) (comprising SEQ ID NOS: 14 and 15) compared favorably with Oligofectamine and lipofectamine 2000 as a carrier of siRNA into SVR-bag4 cells; H$^3$K8b(+RGD) (comprising SEQ ID NOS: 14 and 15) and Lipofectamine 2000 as carriers of siRNA reduced β-gal by 81.9±0.1% and 74.2±0.4%, respectively (P=0.053; Mann-Whitney rank sum test).

While the invention has been described by means of specific embodiments and applications thereof, numerous modifications and variations may be made without departing from the spirit and scope of the invention. The scope of the appended claims is not to be limited to the specific embodiments described.

---

What is claimed is:

1. A method of transfecting cells with siRNA comprising contacting a transfection complex with one or more cells; wherein the transfection complex comprises siRNA and one or more transport polymers selected from the group consisting of $H^3K8b$ (comprising SEQ ID NO: 14), $H^3K8b(+RGD)$ (comprising SEQ ID NO: 14 and SEQ ID NO: 15), $(-HHHK)H^3K8b$ (comprising SEQ ID NO: 16 and SEQ ID NO: 17), and $(-HHHK)H^3K8b(+RGD)$ (comprising SEQ ID NO: 16 and SEQ ID NO: 17).

2. The method of claim 1, wherein the transport polymer comprises at least one stabilizing agent.

3. The method of claim 2, wherein the stabilizing agent comprises PEG.

4. The method of claim 2, wherein the stabilizing agent comprises a hydrophilic polymer.

5. The method of claim 1, wherein the transport polymer comprises a targeting ligand.

6. The method of claim 1, wherein the polymer comprises $H^3K8b$ (comprising SEQ ID NO: 14).

7. The method of claim 1, wherein the polymer comprises $H^3K8b$ (+RGD) (comprising SEQ ID NO: 14 and SEQ ID NO: 15).

8. The method of claim 1, wherein the polymer comprises $(-HHHK)H^3K8b$ (comprising SEQ ID NO: 16 and SEQ ID NO: 17).

9. The method of claim 1, wherein the polymer comprises $(-HHHK)H^3K8b(+RGD)$ (comprising SEQ ID NO: 16 and SEQ ID NO: 17).

10. The method of claim 1, wherein the one or more cells comprise one or more cells selected from the group consisting of transformed, recombinant, malignant, and primary cell lines.

11. The method of claim 1, wherein the one or more cells comprise one or more cells selected from the group consisting of SVR-bag4, MDA-MB-435, C6 and HUVEC cell lines.

12. The method of claim 1, wherein the siRNA targets the Raf-1 sequence.

13. A method of transfecting cells with siRNA comprising mixing siRNA with at least one transport polymer selected from the group consisting of $H^3K8b$ (comprising SEQ ID NO: 14), $H^3K8b(+RGD)$ (comprising SEQ ID NO: 14 and SEQ ID NO: 15), $(-HHHK)H^3K8b$ (comprising SEQ ID NO: 16 and SEQ ID NO: 17), and $(-HHHK)H^3K8b(+RGD)$ (comprising SEQ ID NO: 16 and SEQ ID NO: 17), to form a transfection complex;
  allowing the transfection complex to stand for about 15 minutes to about 1½ hours at approximately room temperature; and
  contacting the transfection complex with one or more cells.

* * * * *

SEQUENCE LISTING

<160> NUMBER OF SEQ ID NOS: 24

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
aauguccaca uggucagcac c                                                   21

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 2
cuuacgcuga guacuucgat t                                                   21

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 3
ucgaaguacu cagccuaagt t                                           21

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cttacgctga gtacttcg                                               18

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
caguugcgca gccugaaugt t                                           21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
caguugcgca gccugaatgt t                                           21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
aacaguugcg cagccugaau g                                           21

<210> SEQ ID NO 8
<211> LENGTH: 21
<212> TYPE: DNA

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 8
cguacgcgga auacuucgat t                                             21

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 9
tcgaaguauu ccgcguacgt t                                             21

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

His His His His Asn His His His His
1               5

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His His His Lys His His His Lys His His His Lys His His His Lys
1               5                   10                  15

His His His

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His His His Lys
1

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
                               peptide

<400> SEQUENCE: 13

His His Lys His His
1               5

<210> SEQ ID NO 14
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys His His His Lys His His His Lys His His His Lys His His His
1               5                   10                  15

His His His Lys His His His Lys His His His Lys His His His Lys
            20                  25                  30

His His His His Asn His His His His
        35                  40

<210> SEQ ID NO 15
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys His His His Lys His His His Lys His His His Lys His His His
1               5                   10                  15

His His His Lys His His His Lys His His His Lys His His His Lys
            20                  25                  30

His His His His Asn His His His His Arg Gly Asp
        35                  40                  45

<210> SEQ ID NO 16
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

His His His Lys His His His Lys His His His His His His Lys His
1               5                   10                  15

His His Lys His His His Lys His His His Asn His His His
            20                  25                  30

His

<210> SEQ ID NO 17
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys His His His Lys His His His Lys His His His His His His Lys
1               5                   10                  15
```

His His His Lys His His His Lys His His His Asn His His His
            20                  25                  30

His His

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

His His His Lys His His His Lys His His His Lys His His His
1               5                   10                  15

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

His His His Lys His His His Lys His His His
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys His His His Lys His His His Lys His His Lys His His His
1               5                   10                  15

Lys

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys His Lys His His Lys His His Lys His His Lys His His Lys His
1               5                   10                  15

His Lys His Lys
            20

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys His Lys His Lys His Lys His Lys His Lys His Lys His Lys His

```
                    5                   10                  15
Lys His Lys

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

His His His Lys His His His Lys His His Lys His His His Lys
1               5                   10                  15

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

His His His Lys His His His Lys His His His Lys
1               5                   10
```